United States Patent
Kaplan et al.

(10) Patent No.: US 10,626,466 B2
(45) Date of Patent: *Apr. 21, 2020

(54) **COMPOSITIONS, KITS AND RELATED METHODS FOR THE DETECTION AND/OR MONITORING OF *PSEUDOMONAS AERUGINOSA***

(71) Applicant: Gen-Probe Incorporated, San Diego, CA (US)

(72) Inventors: Shannon K. Kaplan, San Diego, CA (US); Kristin Livezey, Encinitas, CA (US); Jennifer J. Bungo, San Diego, CA (US); James J. Hogan, Coronado, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 116 days.

This patent is subject to a terminal disclaimer.

(21) Appl. No.: 14/581,919

(22) Filed: Dec. 23, 2014

(65) Prior Publication Data

US 2015/0111212 A1 Apr. 23, 2015

Related U.S. Application Data

(63) Continuation of application No. 12/061,438, filed on Apr. 2, 2008, now Pat. No. 8,927,703.

(60) Provisional application No. 60/909,687, filed on Apr. 2, 2007.

(51) Int. Cl.
*C12Q 1/689* (2018.01)

(52) U.S. Cl.
CPC .................. *C12Q 1/689* (2013.01)

(58) Field of Classification Search
None
See application file for complete search history.

(56) References Cited

U.S. PATENT DOCUMENTS

| | | | |
|---|---|---|---|
| 4,486,539 A | 12/1984 | Ranki et al. | |
| 4,581,333 A | 4/1986 | Kourilsky et al. | |
| 4,683,195 A | 7/1987 | Mullis et al. | |
| 4,683,202 A | 7/1987 | Mullis | |
| 4,751,177 A | 6/1988 | Stabinsky | |
| 4,800,159 A | 1/1989 | Mullis et al. | |
| 4,894,324 A | 1/1990 | Himmelmann et al. | |
| 4,965,188 A | 10/1990 | Mullis et al. | |
| 5,030,557 A | 7/1991 | Hogan et al. | |
| 5,118,801 A | 6/1992 | Lizardi et al. | |
| 5,130,238 A | 7/1992 | Malek et al. | |
| 5,185,439 A | 2/1993 | Arnold, Jr. et al. | |
| 5,270,184 A | 12/1993 | Walker et al. | |
| 5,288,609 A | 2/1994 | Engelhardt et al. | |
| 5,312,728 A | 5/1994 | Lizardi et al. | |
| 5,399,491 A | 3/1995 | Kacian et al. | |
| 5,455,166 A | 10/1995 | Walker | |
| 5,480,784 A | 1/1996 | Kacian et al. | |
| 5,539,082 A | 7/1996 | Nielsen et al. | |
| 5,547,842 A | 8/1996 | Hogan et al. | |
| 5,582,993 A | 12/1996 | Stackebrandt et al. | |
| 5,585,481 A | 12/1996 | Arnold, Jr. et al. | |
| 5,639,599 A | 6/1997 | Ryder et al. | |
| 5,639,604 A | 6/1997 | Arnold, Jr. et al. | |
| 5,656,207 A | 8/1997 | Woodhead et al. | |
| 5,658,737 A | 8/1997 | Nelson et al. | |
| 5,731,148 A | 3/1998 | Becker et al. | |
| 5,747,252 A * | 5/1998 | Yang .................... | C12Q 1/689 435/6.15 |
| 5,786,208 A | 7/1998 | Clark et al. | |
| 5,925,517 A | 7/1999 | Tyagi et al. | |
| 5,948,899 A | 9/1999 | Arnold, Jr. et al. | |
| 6,004,745 A | 12/1999 | Arnold, Jr. et al. | |
| 6,031,091 A | 2/2000 | Arnold, Jr. et al. | |
| 6,060,237 A | 5/2000 | Nygren et al. | |
| 6,074,826 A * | 6/2000 | Hogan ................... | C12Q 1/689 435/6.16 |
| 6,110,678 A | 8/2000 | Weisburg et al. | |
| 6,130,038 A | 10/2000 | Becker et al. | |
| 6,268,490 B1 | 7/2001 | Imanishi et al. | |
| 6,361,945 B1 | 3/2002 | Becker et al. | |
| 6,414,152 B1 | 7/2002 | Campbell et al. | |
| 6,534,273 B2 | 3/2003 | Weisburg et al. | |
| 6,670,461 B1 | 12/2003 | Wengel et al. | |
| 6,835,542 B2 | 12/2004 | Becker et al. | |
| 6,849,412 B2 | 2/2005 | Becker et al. | |
| 7,009,041 B1 * | 3/2006 | McDonough .......... | C07K 14/35 435/6.12 |
| 7,081,527 B2 | 7/2006 | Cunningham et al. | |
| 2003/0032051 A1 | 2/2003 | Gentile-Davey et al. | |
| 2004/0121312 A1 * | 6/2004 | Ecker ................... | C12Q 1/6844 435/5 |
| 2006/0046246 A1 | 3/2006 | Zeng et al. | |
| 2006/0046265 A1 | 3/2006 | Becker et al. | |
| 2006/0068417 A1 | 3/2006 | Becker et al. | |
| 2007/0059735 A1 * | 3/2007 | Cunningham ......... | C12Q 1/689 435/6.15 |

FOREIGN PATENT DOCUMENTS

| | | |
|---|---|---|
| EP | 0370694 A2 | 11/1989 |
| WO | 00/52203 A2 | 9/2000 |
| WO | 00/66789 A2 | 11/2000 |
| WO | 03/095677 A1 | 11/2003 |
| WO | 2007/023461 A2 | 3/2007 |

OTHER PUBLICATIONS

Gutell et al. A compilation of large subunit (23S and 23S-like) ribosomal RNA structures: 1993. Nucleic Acids Research 21(13):3055-3074. (Year: 1993).*
GenBank NR_103960 [online] Feb. 3, 2015 [retrieved on Apr. 23, 2018] retrieved from: https://www.ncbi.nlm.nih.gov/nuccore/NR_103960.1 (Year: 2015).*
Hill, C. Molecular diagnostic testing for infectious diseases using TMA technology. Expert Rev. Diagn. 1(4):445-455. (Year: 2001).*

(Continued)

*Primary Examiner* — Samuel C Woolwine
(74) *Attorney, Agent, or Firm* — Alston & Bird, LLP

(57) ABSTRACT

The present invention provides compositions, methods and kits for the species-specific detection of *Pseudomonas aeruginosa*.

38 Claims, 1 Drawing Sheet

Specification includes a Sequence Listing.

(56) References Cited

OTHER PUBLICATIONS

McDonough et al. Application of Transcription-Mediated Amplification to Detection of Nucleic Acids from Clinically Relevant Organisms. in: Nucleic Acid Amplification Technologies: Application to Disease Diagnosis, edited by Lee, Morse & Olsvik; pp. 113-123. (Year: 1997).*

RNAfold WebServer analysis of SEQ ID No. 54, generated May 20, 2019 (5 pages). (Year: 2019).*

Amagliani et al. Development of a magnetic capture hybridization-PeR assay for Listeria monocytogenes direct detection in milk samples. Journal of Applied Microbiology 100:275-383 (2006).

Caruthers et al., "Chemical Synthesis ofDeoxyoligonucleotides by the Phosphoramidite Method," Methods in Enzymology 154:287-313, 1987.

Elsholz et al., "Automated Detection and Quantitation o ±Bacterial RNA by Using Electrical Microarrays," Anal. Chem. 78:4794-4802, 2006.

GenBank:Accession No. V00331, Mar. 18, 1991.

GenBank GI: 110227054 [online] Mar. 5, 2010 [retrieved on May 18, 2010] retrieved from: http://www.ncbi.nlm.nih.gov/nuccore/110227054 (pp. 1, 249, 1590, 1744, 1997, 2406, 2407, 4288, 4289, 4508, 4509, 4867, 4868).

GenBank GI:45420 [online] Mar. 18, 1991 [retrieved on May 18, 2010] retrieved from: http://www.ncbi.nlm.nih.gov/nuccore/45420.

Guatelli et al., "Isothermal, in vitro amplification of nucleic acids by a multienzyme reaction modeled after retroviral replication," Proc. Natl. Acad. Sci. USA 87:1874-1878, 1990.

Kwoh et al., "Transcription-based amplification system and detection of amplified human immunodeficiency virus type 1 with a bead-based sandwich hybridization format," Proc. Natl. Acad. Sci. USA 86:1173-1177, 1989.

Lizardi et al., "Exponential Amplification of Recombinant-RNA Hybridization Probes," BiotechnolORY 6:1197-1202, 1988.

Ludwig et al., "PCR-Based Preparation of23S rRNA-Targeted Group-Speicific Polynucleotide Probes," 60(9):3236-3244, 1994.

Majlessi et al., "Advantages of 2'-0-methyl oligoribonucleotide probes for detecting RNA targets," Nucleic Acids Research 26(9):2224-2229, 1998.

Persing, David H., "In Vitro Nucleic Acid Amplification Techniques," in Diagnostic Medical Microbiology: Principles and Applications (Persing et al., Eds.), pp. 51-87 (American Society for Microbiology, Washington, DC), 1993.

Peterson et al., "The conformations of locked nucleic acids (LNA)," J Mol. Recognit. 13:44-53, 2000.

Schwartz et al. Real-time PCR detection of Pseudomonas aeruginosa in clinical and municipal wastewater and genotyping of the ciprofloxacin-resistant isolates. FEMS Microbial Ecol57:158-167, Feb. 24, 2006.

Walker et al., "Isothermal in vitro amplification of DNA by a restriction enzyme/DNA polymerase system," Proc. Natl. Acad. Sci. USA 89:392-396, 1992.

Weiss, Rick, "Hot Prospect for New Gene Amplifier—Ligase chain reaction, a combination of DNA amplifier and genetic screen, could do for DNA diagnostics what PCR has done for basic molecular biology," Science 254:1292-1293, 1991.

M. Zuker. Mfold web server for nucleic acid folding and hybridization prediction. Nucleic Acids Res. 31 (13), 3406-3415, 2003.

* cited by examiner

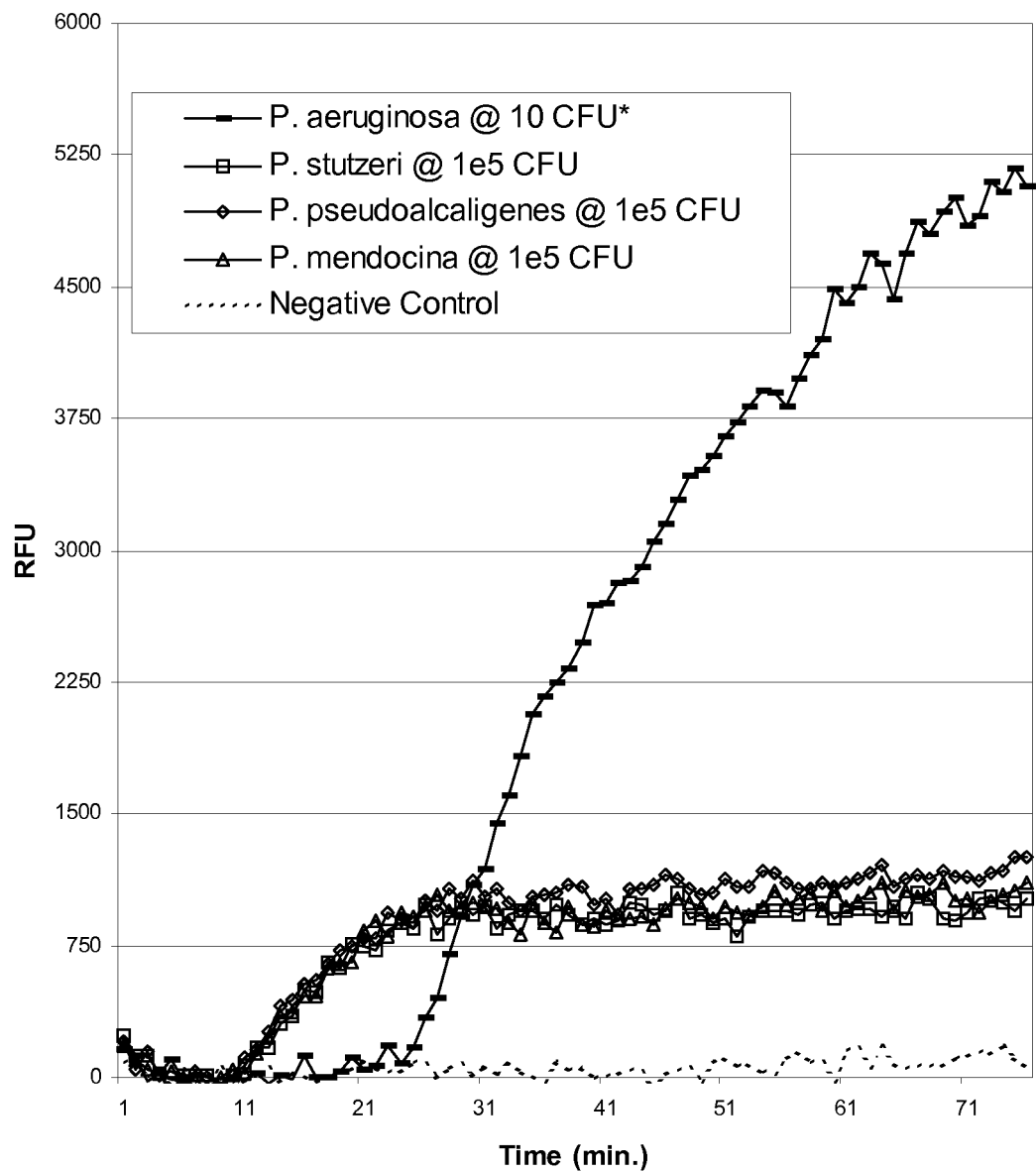

SEQUENCE LISTING

<160> NUMBER OF SEQ ID NOS: 73

<210> SEQ ID NO 1
<211> LENGTH: 53
<212> TYPE: DNA
<213> ORGANISM: Artificial Sequence
<220> FEATURE:
<223> OTHER INFORMATION: Amplification and detection oligonucleotide -continued

```
<220> FEATURE:
<221> NAME/KEY: modified_base
<222> LOCATION: 53
<223> OTHER INFORMATION: blocking moiety

<400> SEQUENCE: 1
aatttaatac gactcactat agggagagaa cccactcccg ttgaaaaggt agg          53

<210> SEQ ID NO 2
<211> LENGTH: 55
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 55
<223> OTHER INFORMATION: Blocking moiety

<400> SEQUENCE: 2
aatttaatac gactcactat agggagacgt tgaaaaggta ggggatgact tgtgg         55

<210> SEQ ID NO 3
<211> LENGTH: 60
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 60
<223> OTHER INFORMATION: Blocking moiety

<400> SEQUENCE: 3
aatttaatac gactcactat agggagagga tgacttgtgg atcggagtga aaggctaatc    60

<210> SEQ ID NO 4
<211> LENGTH: 57
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 57
<223> OTHER INFORMATION: Blocking moiety

<400> SEQUENCE: 4
aatttaatac gactcactat agggagagtg gatcggagtg aaaggctaat caagctc       57

<210> SEQ ID NO 5
<211> LENGTH: 60
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 60
<223> OTHER INFORMATION: Blocking moiety

<400> SEQUENCE: 5
aatttaatac gactcactat agggagatcg gagtgaaagg ctaatcaagc tcggagatag    60

<210> SEQ ID NO 6
<211> LENGTH: 56
<212> TYPE: DNA
<213> ORGANISM: Artificial Sequence
```

```
<220> FEATURE:
<223> OTHER INFORMATION: Amplification and detection oligonucleotide
<220> FEATURE:
<221> NAME/KEY: modified_base
<222> LOCATION: 56
<223> OTHER INFORMATION: Blocking moiety

<400> SEQUENCE: 6
aatttaatac gactcactat agggagatcg gagtgaaagg ctaatcaagc tcggag            56

<210> SEQ ID NO 7
<211> LENGTH: 60
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 60
<223> OTHER INFORMATION: Blocking moiety

<400> SEQUENCE: 7
aatttaatac gactcactat agggagagag tgaaaggcta atcaagctcg gagatagctg        60

<210> SEQ ID NO 8
<211> LENGTH: 56
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 56
<223> OTHER INFORMATION: Blocking moiety

<400> SEQUENCE: 8
aatttaatac gactcactat agggagaggc taatcaagct cggagatagc tggttc            56

<210> SEQ ID NO 9
<211> LENGTH: 59
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 59
<223> OTHER INFORMATION: Blocking moiety

<400> SEQUENCE: 9
aatttaatac gactcactat agggagaggc taatcaagct cggagatagc tggttctcc         59

<210> SEQ ID NO 10
<211> LENGTH: 59
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 59
<223> OTHER INFORMATION: Blocking moiety

<400> SEQUENCE: 10
aatttaatac gactcactat agggagaatc aagctcggag atagctggtt ctcctcgaa         59
```

```
<210> SEQ ID NO 11
<211> LENGTH: 56
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 56
<223> OTHER INFORMATION: Blocking moiety

<400> SEQUENCE: 11
aatttaatac gactcactat agggagactc ggagatagct ggttctcctc gaaagc        56

<210> SEQ ID NO 12
<211> LENGTH: 59
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 59
<223> OTHER INFORMATION: Blocking moiety

<400> SEQUENCE: 12
aatttaatac gactcactat agggagagga gatagctggt tctcctcgaa agctattta    59

<210> SEQ ID NO 13
<211> LENGTH: 58
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 58
<223> OTHER INFORMATION: Blocking moiety

<400> SEQUENCE: 13
aatttaatac gactcactat agggagaagc tggttctcct cgaaagctat ttaggtag     58

<210> SEQ ID NO 14
<211> LENGTH: 46
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 46
<223> OTHER INFORMATION: Blocking moiety

<400> SEQUENCE: 14
aatttaatac gactcactat agggagagct ggttctcctc gaaagc                  46

<210> SEQ ID NO 15
<211> LENGTH: 25
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 15
ccuagccgaa acagttgctc taccc                                         25
```

```
<210> SEQ ID NO 16
<211> LENGTH: 30
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 16
gucgggatga cccectagcc gaaacagttg                                              30

<210> SEQ ID NO 17
<211> LENGTH: 27
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 17
gucgggatga cccectagcc gaaacag                                                 27

<210> SEQ ID NO 18
<211> LENGTH: 29
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 18
gguaagucgg gaugacccccc tagccgaaa                                              29

<210> SEQ ID NO 19
<211> LENGTH: 24
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 19
cgguuuggua agucgggaug accc                                                    24

<210> SEQ ID NO 20
<211> LENGTH: 27
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 20 guaucggag tttgcatcgg tttggta                                                  27

<210> SEQ ID NO 21
<211> LENGTH: 31
<212> TYPE: DNA
<213> ORGANISM: Artificial Sequence
<220> FEATURE:
<223> OTHER INFORMATION: Amplification and detection oligonucleotide

<400> SEQUENCE: 21
cttctgggta ttcggagttt gcatcggttt g                                            31
```

<210> SEQ ID NO 22
<211> LENGTH: 26
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 22
ccaugctcgg cacttctggg tattcg                                          26

<210> SEQ ID NO 23
<211> LENGTH: 27
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 23
augctcggca cttctgggta ttcggag                                         27

<210> SEQ ID NO 24
<211> LENGTH: 27
<212> TYPE: DNA
<213> ORGANISM: Artificial Sequence
<220> FEATURE:
<223> OTHER INFORMATION: Amplification and detection oligonucleotide

<400> SEQUENCE: 24
gtgtgtctcc catgctcggc acttctg                                         27

<210> SEQ ID NO 25
<211> LENGTH: 21
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 21
<223> OTHER INFORMATION: Blocking moiety

<400> SEQUENCE: 25
cgguccucca gucaguguua c                                               21

<210> SEQ ID NO 26
<211> LENGTH: 19
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 19
<223> OTHER INFORMATION: Blocking moiety

<400> SEQUENCE: 26
gguucggucc uccagucag                                                  19

<210> SEQ ID NO 27
<211> LENGTH: 20
<212> TYPE: RNA
<213> ORGANISM: Artificial Sequence
<220> FEATURE:
<223> OTHER INFORMATION: Amplification and detection oligonucleotide

```
<220> FEATURE:
<221> NAME/KEY: modified_base
<222> LOCATION: 20
<223> OTHER INFORMATION: Blocking moiety

<400> SEQUENCE: 27
gaguggguuc gguccuccag                                                     20

<210> SEQ ID NO 28
<211> LENGTH: 20
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 20
<223> OTHER INFORMATION: Blocking moiety

<400> SEQUENCE: 28
gggagugggu ucgguccucc                                                     20

<210> SEQ ID NO 29
<211> LENGTH: 19
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 19
<223> OTHER INFORMATION: Blocking moiety

<400> SEQUENCE: 29
caacgggagu ggguucggu                                                      19

<210> SEQ ID NO 30
<211> LENGTH: 21
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 21
<223> OTHER INFORMATION: Blocking moiety

<400> SEQUENCE: 30
cuuuucaacg ggaguggguu c                                                   21

<210> SEQ ID NO 31
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 31 caucccuac cuuuucaacg ggagu                                                25

<210> SEQ ID NO 32
<211> LENGTH: 20
<212> TYPE: RNA
<213> ORGANISM: Artificial Sequence
```

```
<220> FEATURE:
<223> OTHER INFORMATION: Amplification and detection oligonucleotide
<220> FEATURE:
<221> NAME/KEY: modified_base
<222> LOCATION: 20
<223> OTHER INFORMATION: Blocking moiety

<400> SEQUENCE: 32
cuaccuuuuc aacgggagug                                              20

<210> SEQ ID NO 33
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 33
uccacaaguc auccccuacc uuuuc                                        25

<210> SEQ ID NO 34
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 34
uccgauccac aagucauccc cuacc                                        25

<210> SEQ ID NO 35
<211> LENGTH: 24
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 24
<223> OTHER INFORMATION: Blocking moiety

<400> SEQUENCE: 35
cuccgaucca caagucaucc ccua                                         24

<210> SEQ ID NO 36
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 36
cacuccgauc cacaagucau ccccu                                        25
```

```
<210> SEQ ID NO 37
<211> LENGTH: 23
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 23
<223> OTHER INFORMATION: Blocking moiety

<400> SEQUENCE: 37
ucacuccgau ccacaaguca ucc                                              23

<210> SEQ ID NO 38
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 38
uagccuuuca cuccgaucca caagu                                            25

<210> SEQ ID NO 39
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 39
cuugauuagc cuuucacucc gaucc                                            25

<210> SEQ ID NO 40
<211> LENGTH: 26
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 26
<223> OTHER INFORMATION: Blocking moiety

<400> SEQUENCE: 40
ccgagcuuga uuagccuuuc acuccg                                           26

<210> SEQ ID NO 41
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 41
ucuccgagcu ugauuagccu uucac                                            25
```

```
<210> SEQ ID NO 42
<211> LENGTH: 25
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 42
ccagcuaucu ccgagcuuga uuagc                                          25

<210> SEQ ID NO 43
<211> LENGTH: 27
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 27
<223> OTHER INFORMATION: Blocking moiety

<400> SEQUENCE: 43
ggatgacttg tggatcggag tgaaagg                                        27

<210> SEQ ID NO 44
<211> LENGTH: 27
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 27
<223> OTHER INFORMATION: Blocking moiety

<400> SEQUENCE: 44
atcggagtga aaggctaatc aagctcg                                        27

<210> SEQ ID NO 45
<211> LENGTH: 25
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 25
<223> OTHER INFORMATION: Blocking moiety

<400> SEQUENCE: 45
ctggttctcc tcgaaagcta tttag                                          25

<210> SEQ ID NO 46
<211> LENGTH: 24
<212> TYPE: RNA
<213> ORGANISM: Artificial Sequence
<220> FEATURE:
<223> OTHER INFORMATION: Amplification and detection oligonucleotide

<400> SEQUENCE: 46
ccgagugaua caugaggcgc ucgg                                           24
```

-continued

```
<210> SEQ ID NO 47
<211> LENGTH: 26
<212> TYPE: RNA
<213> ORGANISM: Artificial Sequence
<220> FEATURE:
<223> OTHER INFORMATION: Amplification and detection oligonucleotide

<400> SEQUENCE: 47
cccagaguga uacaugaggc gcuggg                                       26

<210> SEQ ID NO 48
<211> LENGTH: 26
<212> TYPE: RNA
<213> ORGANISM: Artificial Sequence
<220> FEATURE:
<223> OTHER INFORMATION: Amplification and detection oligonucleotide

<400> SEQUENCE: 48
cccagaguga uacaugaggc gcuggg                                       26

<210> SEQ ID NO 49
<211> LENGTH: 24
<212> TYPE: RNA
<213> ORGANISM: Artificial Sequence
<220> FEATURE:
<223> OTHER INFORMATION: Amplification and detection oligonucleotide

<400> SEQUENCE: 49
ccagagugau acaugaggcu cugg                                         24

<210> SEQ ID NO 50
<211> LENGTH: 22
<212> TYPE: RNA
<213> ORGANISM: Artificial Sequence
<220> FEATURE:
<223> OTHER INFORMATION: Amplification and detection oligonucleotide

<400> SEQUENCE: 50
gccucagagu gauacaugag gc                                           22

<210> SEQ ID NO 51
<211> LENGTH: 21
<212> TYPE: RNA
<213> ORGANISM: Artificial Sequence
<220> FEATURE:
<223> OTHER INFORMATION: Amplification and detection oligonucleotide

<400> SEQUENCE: 51
cccagaguga uacaugcugg g                                            21

<210> SEQ ID NO 52
<211> LENGTH: 20
<212> TYPE: RNA
<213> ORGANISM: Artificial Sequence
<220> FEATURE:
<223> OTHER INFORMATION: Amplification and detection oligonucleotide

<400> SEQUENCE: 52
cccagaguga uacaucuggg                                              20

<210> SEQ ID NO 53
<211> LENGTH: 19
<212> TYPE: RNA
<213> ORGANISM: Artificial Sequence
<220> FEATURE:
<223> OTHER INFORMATION: Amplification and detection oligonucleotide
```

<400> SEQUENCE: 53
cccagaguga uacacuggg                                            19

<210> SEQ ID NO 54
<211> LENGTH: 18
<212> TYPE: RNA
<213> ORGANISM: Artificial Sequence
<220> FEATURE:
<223> OTHER INFORMATION: Amplification and detection oligonucleotide

<400> SEQUENCE: 54
cccagaguga uaccuggg                                             18

<210> SEQ ID NO 55
<211> LENGTH: 17
<212> TYPE: RNA
<213> ORGANISM: Artificial Sequence
<220> FEATURE:
<223> OTHER INFORMATION: Amplification and detection oligonucleotide

<400> SEQUENCE: 55
cccagaguga uacuggg                                              17

<210> SEQ ID NO 56
<211> LENGTH: 23
<212> TYPE: RNA
<213> ORGANISM: Artificial Sequence
<220> FEATURE:
<223> OTHER INFORMATION: Amplification and detection oligonucleotide

<400> SEQUENCE: 56
cccagaguga uacaugagcu ggg                                       23

<210> SEQ ID NO 57
<211> LENGTH: 23
<212> TYPE: RNA
<213> ORGANISM: Artificial Sequence
<220> FEATURE:
<223> OTHER INFORMATION: Amplification and detection oligonucleotide

<400> SEQUENCE: 57
cuacccccca gagagauggg uag                                       23

<210> SEQ ID NO 58
<211> LENGTH: 17
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 17
<223> OTHER INFORMATION: Blocking moiety

<400> SEQUENCE: 58
cacccacggc caagcgg                                              17

<210> SEQ ID NO 59
<211> LENGTH: 20
<212> TYPE: RNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 20
<223> OTHER INFORMATION: Blocking moiety

<400> SEQUENCE: 59
ggauuuaccu aagauuucag                                                    20

<210> SEQ ID NO 60
<211> LENGTH: 53
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 53
<223> OTHER INFORMATION: Blocking moiety

<400> SEQUENCE: 60
aatttaatac gactcactat agggagaggg tggccaagtt taaggtggta ggc              53

<210> SEQ ID NO 61
<211> LENGTH: 51
<212> TYPE: DNA
<213> ORGANISM: Artificial Sequence
<220> FEATURE:
<223> OTHER INFORMATION: Amplification and detection oligonucleotide
<220> FEATURE:
<221> NAME/KEY: modified_base
<222> LOCATION: 51
<223> OTHER INFORMATION: Blocking moiety

<400> SEQUENCE: 61
aatttaatac gactcactat agggagaggt aaatccgggg tttcaaggcc g                51

<210> SEQ ID NO 62
<211> LENGTH: 21
<212> TYPE: RNA
<213> ORGANISM: Artificial Sequence
<220> FEATURE:
<223> OTHER INFORMATION: Amplification and detection oligonucleotide

<400> SEQUENCE: 62
cgacgacucg ucaucacguc g                                                  21

<210> SEQ ID NO 63
<211> LENGTH: 20
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 63
ggaagcatgg catcaagcac                                                    20

<210> SEQ ID NO 64
<211> LENGTH: 33
<212> TYPE: DNA
<213> ORGANISM: Artificial Sequence
<220> FEATURE:
<223> OTHER INFORMATION: Amplification and detection DNA-RNA hybrid
      oligonucleotide

<400> SEQUENCE: 64
ccuggttacc tgaagcttag aagcttttct tgg                                     33

<210> SEQ ID NO 65
<211> LENGTH: 51
<212> TYPE: DNA
<213> ORGANISM: Artificial Sequence

```
<220> FEATURE:
<223> OTHER INFORMATION: Target capture oligonucleotide
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18
<223> OTHER INFORMATION: n = G, U or T

<400> SEQUENCE: 65
nnnnnnnnnn nnnnnnnntt taaaaaaaaa aaaaaaaaaa aaaaaaaaaa a          51

<210> SEQ ID NO 66
<211> LENGTH: 63
<212> TYPE: DNA
<213> ORGANISM: Artificial Sequence
<220> FEATURE:
<223> OTHER INFORMATION: Target capture oligonucleotide

<400> SEQUENCE: 66
gctcctctac cgcgtcactt acgtgacacc tttaaaaaaa aaaaaaaaaa aaaaaaaaaa    60
aaa                                                                 63

<210> SEQ ID NO 67
<211> LENGTH: 54
<212> TYPE: DNA
<213> ORGANISM: Artificial Sequence
<220> FEATURE:
<223> OTHER INFORMATION: Target capture DNA-RNA hybrid oligonucleotide

<400> SEQUENCE: 67
ccgcgucacu uacgugacac ctttaaaaaa aaaaaaaaaa aaaaaaaaaa aaaa          54

<210> SEQ ID NO 68
<211> LENGTH: 50
<212> TYPE: DNA
<213> ORGANISM: Artificial Sequence
<220> FEATURE:
<223> OTHER INFORMATION: Target capture DNA-RNA hybrid oligonucleotide

<400> SEQUENCE: 68
cuaccgcguc acuuacgttt aaaaaaaaaa aaaaaaaaaa aaaaaaaaaa               50

<210> SEQ ID NO 69
<211> LENGTH: 56
<212> TYPE: DNA
<213> ORGANISM: Artificial Sequence
<220> FEATURE:
<223> OTHER INFORMATION: Target capture DNA-RNA hybrid oligonucleotide

<400> SEQUENCE: 69
gcuccucuac cgcgucacuu acgtttaaaa aaaaaaaaaa aaaaaaaaaa aaaaaa        56

<210> SEQ ID NO 70
<211> LENGTH: 63
<212> TYPE: DNA
<213> ORGANISM: Artificial Sequence
<220> FEATURE:
<223> OTHER INFORMATION: Target capture oligonucleotide

<400> SEQUENCE: 70
cccattgtcg ttactcatgt cagcattcgc tttaaaaaaa aaaaaaaaaa aaaaaaaaaa    60
aaa                                                                 63
```

```
<210> SEQ ID NO 71
<211> LENGTH: 67
<212> TYPE: DNA
<213> ORGANISM: Artificial Sequence
<220> FEATURE:
<223> OTHER INFORMATION: Target capture oligonucleotide

<400> SEQUENCE: 71
gcttttcaca cccattgtcg ttactcatgt cagctttaaa aaaaaaaaaa aaaaaaaaaa      60
aaaaaaa                                                               67

<210> SEQ ID NO 72
<211> LENGTH: 25
<212> TYPE: RNA
<213> ORGANISM: Artificial Sequence
<220> FEATURE:
<223> OTHER INFORMATION: Target capture oligonucleotide
<220> FEATURE:
<221> NAME/KEY: modified_base
<222> LOCATION: 25
<223> OTHER INFORMATION: Blocking moiety

<400> SEQUENCE: 72
cgcagcuucg guguguggu ugagc                                            25

<210> SEQ ID NO 73
<211> LENGTH: 29
<212> TYPE: RNA
<213> ORGANISM: Artificial Sequence
<220> FEATURE:
<223> OTHER INFORMATION: Target capture oligonucleotide
<220> FEATURE:
<221> NAME/KEY: modified_base
<222> LOCATION: 29
<223> OTHER INFORMATION: Blocking moiety

<400> SEQUENCE: 73
cucaacucac cuucacaggc uuacagaac                                       29
```

COMPOSITIONS, KITS AND RELATED METHODS FOR THE DETECTION AND/OR MONITORING OF *PSEUDOMONAS AERUGINOSA*

CROSS-REFERENCE TO RELATED APPLICATION

This application claims the benefit under 35 U.S.C. § 119(e) (pre-AIA) of U.S. Provisional Patent Application No. 60/909,687, filed Apr. 2, 2007. This application is a continuation under 35 U.S.C. 120 (pre-AIA) of U.S. patent application Ser. No. 12/061,438, now allowed. The entire contents of these applications are incorporated herein by reference in their entirety.

BACKGROUND OF THE INVENTION

Field of the Invention

The present invention relates to compositions, methods and kits for the species-specific identification of *Pseudomonas aeruginosa*, which may be present either alone or as a component, large or small, of a homogeneous or heterogeneous mixture of nucleic acids in a sample taken for testing, e.g., for diagnostic testing, for screening of blood products, for microbiological detection in bioprocesses, food, water, industrial or environmental samples, and for other purposes.

Description of the Related Art

The detection and/or quantitation of specific nucleic acid sequences is an important technique for identifying and classifying microorganisms, diagnosing infectious diseases, detecting and characterizing genetic abnormalities, identifying genetic changes associated with cancer, studying genetic susceptibility to disease, measuring response to various types of treatment, and the like. Such procedures are also useful in detecting and quantifying microorganisms in foodstuffs, water, industrial and environmental samples, seed stocks, and other types of material where the presence of specific microorganisms may need to be monitored.

Nucleic acid amplification assays are well suited for the detection of microorganisms in the context of clinical laboratory testing, bioprocess monitoring, or any other setting in which the detection of a specific microorganisms in a particular sample type is desired, by offering high sensitivity and rapid time-to-result relative to conventional microbiological techniques. In addition, amplification methods can be used in the detection of the vast number of microorganisms that are difficult or impossible to culture on synthetic media. Nevertheless, there are limitations associated with these approaches, many stemming from the high level of sensitivity of nucleic acid amplification methods and the resulting amplification of unintended side-products.

*Pseudomonas aeruginosa* is a gram-negative bacteria that infects humans and can be particularly difficult to treat. In addition, this organism is one of several known contaminant organisms in many biopharmaceutical process streams. Therefore, sensitive and rapid methods for detecting and monitoring the presence of *Pseudomonas aeruginosa* and other related organisms are continually being sought. While the rapid and accurate detection and/or quantitation of *Pseudomonas aeruginosa* is highly desirable, it has been difficult to achieve in practice using conventional reagents and techniques. For example, laboratory culture techniques involve incubating samples for 24-48 hours to allow the organisms to multiply to macroscopically detectable levels. Subculture techniques and metabolic assays are then required to distinguish *Pseudomonas aeruginosa* from related pseudomonads and other enteric bacteria and may require an additional 24-48 hours.

Accordingly, there remains a need in the art for a rapid and robust detection system that can specifically and selectively identify *Pseudomonas aeruginosa* in a sample of interest. As describe further herein, the present invention meets these needs and offers other related advantages.

BRIEF SUMMARY OF THE INVENTION

The present invention is drawn generally to compositions, kits and methods used in the detection of *Pseudomonas aeruginosa*, which offer improvements and other advantages in relation to specificity, sensitivity and speed of detection. As discussed further below, the invention has identified a particular region of the *Pseudomonas aeruginosa* 23s rRNA as a preferred target for nucleic acid amplification reactions which provide these improvements and other advantages.

Therefore, according to one aspect of the invention, there are provided compositions for use in a *Pseudomonas aeruginosa* transcription-mediated amplification assay, where the compositions comprise a T7 provider oligonucleotide that targets the complement of a sequence in a region of *Pseudomonas aeruginosa* 23s rRNA corresponding to bases from about 725-825 of *E. coli* 23s rRNA reference sequence (accession no. V00331), and a non-T7 primer oligonucleotide that targets a sequence in a region of *Pseudomonas aeruginosa* 23s rRNA corresponding to bases from about 845-950 of *E. coli* 23s rRNA. As further described and established herein, use of T7 provider oligonucleotides and non-T7 primer oligonucleotides having particularly defined specificities within this region results in improved sensitivity and selectivity in transcription-mediated amplification reactions for the detection of *Pseudomonas aeruginosa*.

In a particular embodiment of this aspect of the invention, the T7 provider targets the complement of a sequence in a region of *Pseudomonas aeruginosa* 23s rRNA corresponding to bases from about 725-775 of *E. coli* 23s rRNA, and the non-T7 primer targets a sequence in a region of *Pseudomonas aeruginosa* 23s rRNA corresponding to bases from about 900-950 of *E. coli* 23s rRNA.

In a more particular embodiment, the T7 provider targets the complement of a sequence in a region of *Pseudomonas aeruginosa* 23s rRNA corresponding to bases from about 739-766 of *E. coli* 23s rRNA, and the non-T7 primer targets a sequence in a region of the *Pseudomonas aeruginosa* 23s rRNA corresponding to bases from about 918-943 of *E. coli* 23s rRNA.

In a more specific embodiment, the T7 provider is selected from SEQ ID NO:2, SEQ ID NO:1, SEQ ID NO:11, or SEQ ID NO:14, and the non-T7 primer is selected from SEQ ID NO:22, SEQ ID NO:24, SEQ ID NO:19, or SEQ ID NO:15, as defined herein.

A particularly preferred composition of the invention comprises the T7 provider SEQ ID NO:2 and the non-T7 primer oligonucleotide SEQ ID NO:24, as defined herein.

In addition to the T7 provider oligonucleotides and non-T7 primer oligonucleotides discussed above, the compositions according to the invention can further comprise one or more additional oligonucleotide types and/or other amplification reagents that serve to facilitate or improve one or more aspects of the transcription-mediated amplification reaction, such as detection oligonucleotides, extend oligonucleotides, blocker oligonucleotides and the like.

For example, in one embodiment, the compositions of the invention will further comprise a detection oligonucleotide, preferably a torch oligonucleotide or molecular beacon. In a particular embodiment, the detection oligonucleotide is a torch oligonucleotide selected from SEQ ID NO:51, SEQ ID NO:54, SEQ ID NO:50, or SEQ ID NO:56, as defined herein.

The compositions of the invention may also further comprise an extend oligonucleotide. In a particular embodiment, the extend oligonucleotide is selected from SEQ ID NO:43 or SEQ ID NO:44, as defined herein.

The compositions of the invention may also further comprise a blocker oligonucleotide. In a particular embodiment, the blocker oligonucleotide is selected from SEQ ID NO:29, SEQ ID NO:26, SEQ ID NO:40, or SEQ ID NO:42, as defined herein.

In one preferred embodiment of the invention, the composition comprises the T7 provider oligonucleotide SEQ ID NO:2 and the non-T7 primer oligonucleotide SEQ ID NO:24, and optionally further comprising blocker oligonucleotide SEQ ID NO:29, the torch oligonucleotide SEQ ID NO:54, the extend oligonucleotide SEQ ID NO:44, the target capture oligonucleotide SEQ ID NO:68 and, optionally, the target capture helper oligonucleotide SEQ ID NO:73, as defined herein.

According to another aspect of the invention, there are provided kits for performing a *Pseudomonas aeruginosa* transcription-mediated amplification assay, where the kits comprise a T7 provider oligonucleotide that targets the complement of a sequence in a region of *Pseudomonas aeruginosa* 23s rRNA corresponding to bases from about 725-825 of *E. coli* 23s rRNA, and a non-T7 primer oligonucleotide that targets a sequence in a region of *Pseudomonas aeruginosa* 23s rRNA corresponding to bases from about 845-950 of *E. coli* 23s rRNA.

In a particular embodiment of this aspect of the invention, the T7 provider targets the complement of a sequence in a region of *Pseudomonas aeruginosa* 23s rRNA corresponding to bases from about 725-775 of *E. coli* 23s rRNA, and the non-T7 primer targets a sequence in a region of the *Pseudomonas aeruginosa* 23s rRNA corresponding to bases from about 900-950 of *E. coli* 23s rRNA.

In another particular embodiment, the T7 provider targets the complement of a sequence in a region of the *Pseudomonas aeruginosa* 23s rRNA corresponding to bases from about 739-766 of *E. coli* 23s rRNA, and the non-T7 primer targets a sequence in a region of the *Pseudomonas aeruginosa* 23s rRNA corresponding to bases from about 918-943 of *E. coli* 23s rRNA.

In a more specific embodiment, the T7 provider is selected from SEQ ID NO:2, SEQ ID NO:1, SEQ ID NO:11, or SEQ ID NO:14, and the non-T7 primer is selected from SEQ ID NO:22, SEQ ID NO:24, SEQ ID NO:19, or SEQ ID NO:15.

In another specific embodiment, the T7 provider is SEQ ID NO:2 and the non-T7 primer is SEQ ID NO:24.

The kits of the invention may further comprise, in addition to the T7 provider oligonucleotide and non-T7 primer oligonucleotide, one of more additional oligonucleotides and/or other reagents that are desired or preferred in a transcription-mediated amplification reaction, such as detection oligonucleotides, extend oligonucleotides, blocker oligonucleotides and the like. For example, a kit of the invention may further comprise a detection oligonucleotide, such as a torch oligonucleotide or molecular beacon. In a particular embodiment, for example, the kit comprises a torch oligonucleotide that is selected from SEQ ID NO:51, SEQ ID NO:54, SEQ ID NO:50, or SEQ ID NO:56.

A kit of the invention may also further comprise an extend oligonucleotide. In a particular embodiment, the extend oligonucleotide is selected from SEQ ID NO:43 or SEQ ID NO:44.

A kit of the invention may also further comprise a blocker oligonucleotide. In a particular embodiment, the blocker oligonucleotide is selected from SEQ ID NO:29, SEQ ID NO:26, SEQ ID NO:40, or SEQ ID NO:42.

In a more specific embodiment, a kit of the invention comprises the T7 provider oligonucleotide, SEQ ID NO:2 and the non-T7 primer oligonucleotide, SEQ ID NO:24, and optionally further comprising blocker oligonucleotide SEQ ID NO:29, the torch oligonucleotide SEQ ID NO:54, the extend oligonucleotide SEQ ID NO:44, the target capture oligonucleotide SEQ ID NO:69 and, optionally, the target capture helper oligonucleotide SEQ ID NO:73.

According to yet another aspect of the invention, there are provided methods for detecting the presence of *Pseudomonas aeruginosa* in a sample, wherein the method involves performing a transcription-mediated amplification assay using a T7 provider oligonucleotide and a non-T7 primer oligonucleotide, wherein the T7 provider oligonucleotide targets the complement of a sequence in a region of *Pseudomonas aeruginosa* 23s rRNA corresponding to bases from about 725-825 of *E. coli* 23s rRNA, and the non-T7 primer oligonucleotide targets a sequence in a region of *Pseudomonas aeruginosa* 23s rRNA corresponding to bases from about 845-950 of *E. coli* 23s rRNA.

In a particular embodiment, the T7 provider targets the complement of a sequence in a region of *Pseudomonas aeruginosa* 23s rRNA corresponding to bases from about 725-775 of *E. coli* 23s rRNA, and the non-T7 primer targets a sequence in a region of *Pseudomonas aeruginosa* 23s rRNA corresponding to bases from about 900-950 of *E. coli* 23s rRNA.

In another particular embodiment, the T7 provider targets the complement of a sequence in a region of *Pseudomonas aeruginosa* 23s rRNA corresponding to bases from about 739-766 of *E. coli* 23s rRNA, and the non-T7 primer targets a sequence of a region of the *Pseudomonas aeruginosa* 23s rRNA corresponding to bases from about 918-943 of *E. coli* 23s rRNA.

In a more specific embodiment, the T7 provider is selected from SEQ ID NO:2, SEQ ID NO:1, SEQ ID NO:11 or SEQ ID NO:14, and the non-T7 primer is selected from SEQ ID NO:22, SEQ ID NO:24, SEQ ID NO:19 or SEQ ID NO:15.

In another more specific embodiment, the T7 provider is SEQ ID NO:2 and the non-T7 primer is SEQ ID NO:24.

As with the compositions and kits discussed above, the methods according to this aspect of the invention may further comprise additional ancillary oligonucleotides and/or reagents effective in a transcription-mediated amplification reaction, such as a detection oligonucleotide, blocker oligonucleotide, extend oligonucleotide, and the like.

For example, the methods may employ the use of a detection oligonucleotide, such as a torch oligonucleotide or molecular beacon. In one embodiment, the torch oligonucleotide is selected from SEQ ID NO:51, SEQ ID NO:54, SEQ ID NO:50 or SEQ ID NO:56.

The methods may also employ the use of an extend oligonucleotide, such as SEQ ID NO:43 or SEQ ID NO:44, or a blocker oligonucleotide such as SEQ ID NO:29, SEQ ID NO:26, SEQ ID NO:40 or SEQ ID NO:42.

In a more specific embodiment of this aspect of the invention, the transcription-mediated amplification method employs the use of the T7 provider oligonucleotide SEQ ID NO:2 and the non-T7 primer oligonucleotide SEQ ID NO:24, and further employ the use of the blocker oligonucleotide SEQ ID NO:29, the torch oligonucleotide SEQ ID NO:54, the extend oligonucleotide SEQ ID NO:44, the target capture oligonucleotide SEQ ID NO:69 and, optionally, the target capture helper oligonucleotide, SEQ ID NO:73.

BRIEF DESCRIPTION OF THE DRAWINGS

FIG. 1 shows a real-time fluorescence signal that was obtained for an amplification of approximately 10 CFU of *P. aeruginosa* compared to that which was obtained for $10^5$ CFU of closely related pseudomonads.

DETAILED DESCRIPTION OF THE INVENTION

The present invention relates generally to compositions, methods and kits for detecting, monitoring and/or quantitating the presence of *Pseudomonas aeruginosa* in samples, such as clinical samples, bioprocess samples, food samples, water samples, industrial samples, environmental samples, or any other sample type known or suspected of containing *Pseudomonas aeruginosa*. Specific compositions, methods and kits of the present invention provide improved sensitivity, specificity and selectivity in the amplification-based detection of *Pseudomonas aeruginosa*.

As a result of extensive analyses of amplification oligonucleotides specific for *Pseudomonas aeruginosa*, the present invention has identified a particular region of *Pseudomonas aeruginosa*, corresponding to the region of *E. coli* 23s rRNA reference sequence (accession no. V00331) from about 700 to 1000 nucleotide bases (hereinafter referred to as the "800 region"), as a preferred target for amplification-based detection of *Pseudomonas aeruginosa*. Accordingly, the present invention relates to amplification oligonucleotides, compositions, reactions mixtures, kits, and the like, as well as their use in the species-specific detection of *Pseudomonas aeruginosa* in a sample of interest.

The terms and concepts of the invention have meanings as set forth herein unless expressly stated to the contrary and/or unless context specifically dictates otherwise. Unless defined otherwise, scientific and technical terms used herein have the same meaning as commonly understood by those skilled in the relevant art. General definitions may be found in technical books relevant to the art of molecular biology, e.g., Dictionary of Microbiology and Molecular Biology, 2nd ed. (Singleton et al., 1994, John Wiley & Sons, New York, N.Y.) or The Harper Collins Dictionary of Biology (Hale & Marham, 1991, Harper Perennial, New York, N.Y.). Unless mentioned otherwise, techniques employed or contemplated herein are standard methodologies well known to one of ordinary skill in the art. The examples included herein illustrate some preferred embodiments.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein. Further, each reference cited herein is specifically incorporated herein by reference in its entirety.

Nucleic Acid Amplification and Detection

It will be understood by the skilled artisan that the preferred oligonucleotides, compositions, reaction mixtures and kits of the present invention are used in nucleic acid amplification methods for the improved detection of *Pseudomonas aeruginosa*. While such methods and techniques are well known and established, illustrative and preferred aspects of nucleic acid amplification, detection, etc., is discussed below.

Nucleic Acids

The term "nucleic acid" is intended to encompass a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, virus genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. Nucleic acids may include modified bases to alter the function or behavior of the nucleic acid, e.g., addition of a 3'-terminal dideoxynucleotide to block additional nucleotides from being added to the nucleic acid. As used herein, a "sequence" of a nucleic acid refers to the sequence of bases which make up a nucleic acid. The term "polynucleotide" may be used herein to denote a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" is a unit which does not significantly participate in hybridization of a polymer. Such units must not, for example, participate in any significant hydrogen bonding with a nucleotide, and would exclude units having as a component one of the five nucleotide bases or analogs thereof.

Target Nucleic Acid/Target Sequence

A "target nucleic acid" is a nucleic acid comprising a "target sequence" to be amplified. Target nucleic acids may be DNA or RNA as described herein, and may be either single-stranded or double-stranded. The target nucleic acid may include other sequences besides the target sequence which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

Target nucleic acids may be isolated from any number of sources based on the purpose of the amplification assay being carried out. Sources of target nucleic acids include, but are not limited to, clinical specimens, e.g., blood, urine, saliva, feces, semen, or spinal fluid, from criminal evidence, from environmental samples, e.g., water or soil samples, from food, from industrial samples, from cDNA libraries, or from total cellular RNA. By "isolated" it is meant that a sample containing a target nucleic acid is taken from its natural milieu, but the term does not connote any degree of purification. If necessary, target nucleic acids of the present invention are made available for interaction with the various oligonucleotides of the present invention. This may include, for example, cell lysis or cell permeabilization to release the target nucleic acid from cells, which then may be followed by one or more purification steps, such as a series of isolation and wash steps. See, e.g., Clark et al., "Method for Extracting Nucleic Acids from a Wide Range of Organisms," U.S. Pat. No. 5,786,208, the contents of which are hereby incorporated by reference herein. This is particularly important where the sample may contain components that can interfere with the amplification reaction, such as, for example, heme present in a blood sample. See Ryder et al., "Amplification of Nucleic Acids from Mononuclear Cells Using Iron Complexing and Other Agents," U.S. Pat. No. 5,639,599, the contents of which are hereby incorporated by reference herein. Methods to prepare target nucleic acids from various sources for amplification are well known to those of ordinary skill in the art. Target nucleic acids of the present invention may be purified to some degree prior to the amplification reactions described herein, but in other cases, the sample is added to the amplification reaction without any further manipulations.

The term "target sequence" refers to the particular nucleotide sequence of the target nucleic acid which is to be amplified. The "target sequence" includes the complexing sequences to which oligonucleotides (e.g., priming oligonucleotides and/or promoter oligonucleotides) complex during the processes of the present invention. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids. As will be understood by those of ordinary skill in the art, "unique" sequences are judged from the testing environment. At least the sequences recognized by the detection probe (as described in more detail elsewhere herein) should be unique in the environment being tested, but need not be unique within the universe of all possible sequences. Furthermore, even though the target sequence should contain a "unique" sequence for recognition by a detection probe, it is not always the case that the priming oligonucleotide and/or promoter oligonucleotide are recognizing "unique" sequences. In some embodiments, it may be desirable to choose a target sequence which is common to a family of related organisms, for example, a sequence which is common to one or more pseudomonads that might be in a sample. In other situations, a very highly specific target sequence, or a target sequence having at least a highly specific region recognized by the detection probe and amplification oligonucleotides, would be chosen so as to distinguish between closely related organisms, for example, between pathogenic and non-pathogenic E. coli. A target sequence of the present invention may be of any practical length. A minimal target sequence includes the region which hybridizes to the priming oligonucleotide (or the complement thereof), the region which hybridizes to the hybridizing region of the promoter oligonucleotide (or the complement thereof), and a region used for detection, e.g., a region which hybridizes to a detection probe, described in more detail elsewhere herein. The region which hybridizes with the detection probe may overlap with or be contained within the region which hybridizes with the priming oligonucleotide (or its complement) or the hybridizing region of the promoter oligonucleotide (or its complement). In addition to the minimal requirements, the optimal length of a target sequence depends on a number of considerations, for example, the amount of secondary structure, or self-hybridizing regions in the sequence. Typically, target sequences of the present invention range from about 100 nucleotides in length to from about 150 to about 250 nucleotides in length. The optimal or preferred length may vary under different conditions which can be determined according to the methods described herein. The term "amplicon" refers to the nucleic acid molecule generated during an amplification procedure that is complementary or homologous to a sequence contained within the target sequence.

Nucleic Acid "Identity"

In certain embodiments, a nucleic acid of the present invention comprises a contiguous base region that is at least 80%, 90%, or 100% identical to a contiguous base region of a reference nucleic acid. For short nucleic acids, e.g., certain oligonucleotides of the present invention, the degree of identity between a base region of a "query" nucleic acid and a base region of a reference nucleic acid can be determined by manual alignment. "Identity" is determined by comparing just the sequence of nitrogenous bases, irrespective of the sugar and backbone regions of the nucleic acids being compared. Thus, the query:reference base sequence alignment may be DNA:DNA, RNA:RNA, DNA:RNA, RNA:DNA, or any combinations or analogs thereof. Equivalent RNA and DNA base sequences can be compared by converting U's (in RNA) to T's (in DNA).

Oligonucleotides & Primers

As used herein, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof. The term oligonucleotide does not denote any particular function to the reagent, rather, it is used generically to cover all such reagents described herein. An oligonucleotide may serve various different functions, e.g., it may function as a primer if it is specific for and capable of hybridizing to a complementary strand and can further be extended in the presence of a nucleic acid polymerase, it may provide a promoter if it contains a sequence recognized by an RNA polymerase and allows for transcription (e.g., a T7 provider), and it may function to prevent hybridization or impede primer extension if appropriately situated and/or modified. Specific oligonucleotides of the present invention are described in more detail below.

As used herein, an oligonucleotide can be virtually any length, limited only by its specific function in the amplification reaction or in detecting an amplification product of the amplification reaction. However, in certain embodiments, preferred oligonucleotides will contain at least about 10, 12, 14, 16, 18 or 20 contiguous bases that are complementary to a region of the target nucleic acid sequence or its complementary strand. The contiguous bases are preferably at least about 80%, more preferably at least about 90%, and most preferably completely complementary to the target sequence to which the oligonucleotide binds. Certain preferred oligonucleotides are of lengths generally between about 10-100, 10-75, 10-50 or 10-25 bases long and optionally can include modified nucleotides.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide of the present invention. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl substitution to the ribofuranosyl moiety. See Becker et al., U.S. Pat. No. 6,130,038. Other sugar modifications include, but are not limited to 2'-amino, 2'-fluoro, (L)-alpha-threofuranosyl, and pentopyranosyl modifications. The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. DNA analogs having a pseudo peptide backbone are commonly referred to as "peptide nucleic acids" or "PNA" and are disclosed by Nielsen et al., "Peptide Nucleic Acids," U.S. Pat. No. 5,539,082. Other linkage modifications include, but are not limited to, morpholino bonds.

Non-limiting examples of oligonucleotides or oligos contemplated by the present invention include nucleic acid analogs containing bicyclic and tricyclic nucleoside and nucleotide analogs (LNAs). See Imanishi et al., U.S. Pat. No. 6,268,490; and Wengel et al., U.S. Pat. No. 6,670,461.) Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions.

While design and sequence of oligonucleotides for the present invention depend on their function as described below, several variables must generally be taken into account. Among the most critical are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to initially screen large numbers of potential oligonucleotides.

The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

As used in this disclosure, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

An oligonucleotide substantially corresponding to a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions.

One skilled in the art will understand that substantially corresponding oligonucleotides of the invention can vary from the referred to sequence and still hybridize to the same target nucleic acid sequence. This variation from the nucleic acid may be stated in terms of a percentage of identical bases within the sequence or the percentage of perfectly complementary bases between the probe or primer and its target sequence. Thus, an oligonucleotide of the present invention substantially corresponds to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557, the contents of which are incorporated by reference herein. Helpers may also be used to assist with the hybridization to target nucleic acid sequences and function of primer, target capture and other oligonucleotides.

Blocking Moiety

As used herein, a "blocking moiety" is a substance used to "block" the 3'-terminus of an oligonucleotide or other nucleic acid so that it cannot be efficiently extended by a nucleic acid polymerase. A blocking moiety may be a small molecule, e.g., a phosphate or ammonium group, or it may be a modified nucleotide, e.g., a 3'2' dideoxynucleotide or 3' deoxyadenosine 5'-triphosphate (cordycepin), or other modified nucleotide. Additional blocking moieties include, for example, the use of a nucleotide or a short nucleotide sequence having a 3'-to-5' orientation, so that there is no free hydroxyl group at the 3'-terminus, the use of a 3' alkyl group, a 3' non-nucleotide moiety (see, e.g., Arnold et al., "Non-Nucleotide Linking Reagents for Nucleotide Probes," U.S. Pat. No. 6,031,091, the contents of which are hereby incorporated by reference herein), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well known to those of ordinary skill in the art.

Priming Oligonucleotide or Primer

A priming oligonucleotide or "primer" is an oligonucleotide, at least the 3'-end of which is complementary to a nucleic acid template, and which complexes (by hydrogen bonding or hybridization) with the template to give a primer:template complex suitable for initiation of synthesis by an RNA- or DNA-dependent DNA polymerase. A priming oligonucleotide is extended by the addition of covalently bonded nucleotide bases to its 3'-terminus, which bases are complementary to the template. The result is a primer extension product. A priming oligonucleotide of the present invention is typically at least 10 nucleotides in length, and may extend up to 15, 20, 25, 30, 35, 40, 50 or more nucleotides in length. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. By its very nature of being extended by a DNA polymerase, a priming oligonucleotide does not comprise a 3'-blocking moiety.

Promoter Oligonucleotide/Promoter Sequence

As is well known in the art, a "promoter" is a specific nucleic acid sequence that is recognized by a DNA-dependent RNA polymerase ("transcriptase") as a signal to bind to the nucleic acid and begin the transcription of RNA at a specific site. For binding, it was generally thought that such transcriptases required DNA which had been rendered double-stranded in the region comprising the promoter sequence via an extension reaction, however, the present inventors have determined that efficient transcription of RNA can take place even under conditions where a double-stranded promoter is not formed through an extension reaction with the template nucleic acid. The template nucleic acid (the sequence to be transcribed) need not be double-stranded. Individual DNA-dependent RNA polymerases recognize a variety of different promoter sequences, which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

As used herein, a "promoter oligonucleotide" or "provider" refers to an oligonucleotide comprising first and second regions, and which is modified to prevent the initiation of DNA synthesis from its 3'-terminus. The "first region" of a promoter oligonucleotide of the present invention comprises a base sequence which hybridizes to a DNA template, where the hybridizing sequence is situated 3', but not necessarily adjacent to, a promoter region. The hybridizing portion of a promoter oligonucleotide of the present invention is typically at least 10 nucleotides in length, and may extend up to 15, 20, 25, 30, 35, 40, 50 or more nucleotides in length. The "second region" comprises a promoter sequence for an RNA polymerase. A promoter oligonucleotide of the present invention is engineered so that it is incapable of being extended by an RNA- or DNA-dependent DNA polymerase, e.g., reverse transcriptase, preferably comprising a blocking moiety at its 3'-terminus as described above. Suitable and preferred promoter oligonucleotides are described herein.

Terminating Oligonucleotide

In the present invention, a "terminating oligonucleotide" or "blocker oligo" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand. A terminating oligonucleotide is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-methyl ribonucleotides. These modified nucleotides have demonstrated higher thermal stability of complementary duplexes. The 2'-O-methyl ribonucleotides also function to increase the resistance of oligonucleotides to exonucleases, thereby increasing the half-life of the modified oligonucleotides. See, e.g., Majlessi et al. (1988) *Nucleic Acids Res.* 26, 2224-9, the contents of which are hereby incorporated by reference herein. Other modifications as described elsewhere herein may be utilized in addition to or in place of 2'-O-methyl ribonucleotides. For example, a terminating oligonucleotide may comprise PNA or an LNA. See, e.g., Petersen et al. (2000) *J. Mol. Recognit.* 13, 44-53, the contents of which are hereby incorporated by reference herein. A terminating oligonucleotide of the present invention typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. A terminating oligonucleotide of the present invention is typically at least 10 bases in length, and may extend up to 15, 20, 25, 30, 35, 40, 50 or more nucleotides in length. Suitable and preferred terminating oligonucleotides are described herein. It should be noted that while a terminating oligonucleotide typically or necessarily includes a 3'-blocking moiety, "3'-blocked" oligonucleotides are not necessarily terminating oligonucleotides. Other oligonucleotides of the present invention, e.g., promoter oligonucleotides and capping oligonucleotides are typically or necessarily 3'-blocked as well.

Extender Oligonucleotide

An "extender oligonucleotide" or "extend oligo" refers to an oligonucleotide that is the same sense as the T7 provider and may act as a helper oligonucleotide that opens up structure or improves specificity. An extender oligonucleotide hybridizes to a DNA template adjacent to or near the 3'-end of the first region of a promoter oligonucleotide. An extender oligonucleotide preferably hybridizes to a DNA template such that the 5'-terminal base of the extender oligonucleotide is within 3, 2 or 1 bases of the 3'-terminal base of a promoter oligonucleotide. Most preferably, the 5'-terminal base of an extender oligonucleotide is adjacent to the 3'-terminal base of a promoter oligonucleotide when the extender oligonucleotide and the promoter oligonucleotide are hybridized to a DNA template. To prevent extension of an extender oligonucleotide, a 3'-terminal blocking moiety is typically included. An extender oligonucleotide is preferably 10 to 50 nucleotides in length, more preferably 20 to 40 nucleotides in length, and most preferably 30 to 35 nucleotides in length {see US2006/0046265}.

Probe

By "probe" or "detection probe" is meant a molecule comprising an oligonucleotide having a base sequence partly or completely complementary to a region of a target sequence sought to be detected, so as to hybridize thereto under stringent hybridization conditions. As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent).

The probes of this invention may have additional nucleosides or nucleobases outside of the targeted region so long as such nucleosides or nucleobases do not substantially affect hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both.

The probes preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester. Certain probes of the present invention do not include a label. For example, non-labeled "capture" probes may be used to enrich for target sequences or replicates thereof, which may then be detected by a second "detection" probe. See, e.g., Weisburg et al., "Two-Step Hybridization and Capture of a Polynucleotide," U.S. Pat. No. 6,534,273, which is hereby incorporated by reference herein. While detection probes are typically labeled, certain detection technologies do not require that the probe be labeled. See, e.g., Nygren et al., "Devices and Methods for Optical Detection of Nucleic Acid Hybridization," U.S. Pat. No. 6,060,237.

By "stable" or "stable for detection" is meant that the temperature of a reaction mixture is at least 2° C. below the melting temperature of a nucleic acid duplex. The temperature of the reaction mixture is more preferably at least 5° C. below the melting temperature of the nucleic acid duplex, and even more preferably at least 10° C. below the melting temperature of the reaction mixture.

By "preferentially hybridize" is meant that under stringent hybridization assay conditions, probes of the present invention hybridize to their target sequences, or replicates thereof, to form stable probe:target hybrids, while at the same time formation of stable probe:non-target hybrids is minimized. Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification.

Probes of a defined sequence may be produced by techniques known to those of ordinary skill in the art, such as by chemical synthesis, and by in vitro or in vivo expression from recombinant nucleic acid molecules. Preferably probes are 10 to 100 nucleotides in length, more preferably 12 to 50 bases in length, and even more preferably 18 to 35 bases in length.

Hybridize/Hybridization

Nucleic acid hybridization is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., Roger L. P. Adams et al., "The Biochemistry Of The Nucleic Acids" ($11^{th}$ ed. 1992).)

"Stringent" hybridization assay conditions refer to conditions wherein a specific detection probe is able to hybridize with target nucleic acids over other nucleic acids present in the test sample. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "preferentially" hybridize is meant that under stringent hybridization assay conditions, certain complementary nucleotides or nucleobase sequences hybridize to form a stable hybrid preferentially over other, less stable duplexes.

Nucleic Acid Amplification

As noted, the present invention relates generally to compositions and methods for detection of *Pseudomonas aeruginosa* in a sample of interest using nucleic acid amplification methods. By "amplification" or "nucleic acid amplification" is meant production of multiple copies of a target nucleic acid that contains at least a portion of the intended specific target nucleic acid sequence, as further described herein. The multiple copies may be referred to as amplicons or amplification products The compositions and methods of the invention may be performed on essentially any sample type of interest that is known or suspected of containing *Pseudomonas aeruginosa*. These may include biological samples, clinical samples, industrial samples, and the like. In one preferred embodiment, the sample is a biopharmaceutical process (bioprocess) stream where *Pseudomonas aeruginosa* is a known or suspected contaminant. A "bioprocess," as used herein, refers generally to any process in which living cells or organisms, or components thereof, are present, either intended or unintended. For example, essentially any manufacturing or other process that employs one or more samples or sample streams, at least one of which contains living cells, organisms, or components thereof, or contains such cells, organisms or components as a result of unintended contamination, is considered a bioprocess. In many such processes it is desirable to have the ability to detect, identify and/or control the presence and/or sources of living cells, organisms or components thereof within a process. Using the methods of the present invention, for example, the presence and/or sources of *Pseudomonas aeruginosa* in one or more bioprocess samples and/or streams may be monitored in a rapid and sensitive fashion.

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA. The ligase chain reaction (Weiss, R. 1991, Science 254: 1292), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product. Another method is strand displacement amplification (Walker, G. et al., 1992, Proc. Natl. Acad. Sci. USA 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315). Other amplification methods include: nucleic acid sequence based amplification (U.S. Pat. No. 5,130,238), commonly referred to as NASBA; one that uses an RNA replicase to amplify the probe molecule itself (Lizardi, P. et al., 1988, BioTechnol. 6: 1197-1202), commonly referred to as Q-β replicase; a transcription based amplification method (Kwoh, D. et al., 1989, Proc. Natl. Acad. Sci. USA 86:1173-1177); self-sustained sequence replication (Guatelli, J. et al., 1990, Proc. Natl. Acad. Sci. USA 87: 1874-1878); and, transcription mediated amplification (U.S. Pat. Nos. 5,480,784 and 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.).

In a preferred embodiment of the invention, *Pseudomonas aeruginosa* is detected by a transcription-based amplification technique. One preferred transcription-based amplification system is transcription-mediated amplification (TMA), which employs an RNA polymerase to produce multiple RNA transcripts of a target region. Exemplary TMA amplification methods are described U.S. Pat. Nos. 5,480,784, 5,399,491, US 2006/0046265, and references cited therein, the contents of which are incorporated herein by reference in their entireties. TMA uses a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In one version of the TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce promoter-primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

Another version of TMA uses one primer and one or more additional amplification oligomers to amplify nucleic acids in vitro, making transcripts (amplicons) that indicate the presence of the target sequence in a sample (previously described in detail in Becker et al., US Pub. No. 2006/0046265, the details of which are hereby incorporated by reference herein). Briefly, the single-primer TMA method uses a primer (or "priming oligomer"), a modified promoter oligomer (or "promoter-provider") that is modified to prevent the initiation of DNA synthesis from its 3' end (e.g., by including a 3'-blocking moiety) and, optionally, a binding molecule (e.g., a 3'-blocked extender oligomer) to terminate elongation of a cDNA from the target strand. This method synthesizes multiple copies of a target sequence and includes the steps of treating a target RNA that contains a target sequence with a priming oligomer and a binding molecule, where the primer hybridizes to the 3' end of the target strand. RT initiates primer extension from the 3' end of the primer to produce a cDNA which is in a duplex with the target strand (e.g., RNA:cDNA). When a binding molecule, such as a 3' blocked extender oligomer, is used in the reaction, it binds to the target nucleic acid adjacent near the 5' end of the target sequence. That is, the binding molecule binds to the target strand next to the 5' end of the target sequence to be amplified. When the primer is extended by DNA polymerase activity of RT to produce cDNA, the 3' end of the cDNA is determined by the position of the binding molecule because polymerization stops when the primer extension product reaches the binding molecule bound to the target strand. Thus, the 3' end of the cDNA is complementary to the 5' end of the target sequence. The RNA:cDNA duplex is separated when RNase (e.g., RNase H of RT) degrades the RNA strand, although those skilled in the art will appreciate that any form of strand separation may be used. Then, the promoter-provider oligomer hybridizes to the cDNA near the 3' end of the cDNA strand. The promoter-provider oligomer includes a 5' promoter sequence for an RNA polymerase and a 3' region complementary to a sequence in the 3' region of the cDNA. The promoter-provider oligomer also has a modified 3' end that includes a blocking moiety that prevents initiation of DNA synthesis from the 3' end of the promoter-provider oligomer. In the promoter-provide:cDNA duplex, the 3'-end of the cDNA is extended by DNA polymerase activity of RT using the promoter oligomer as a template to add a promoter sequence to the cDNA and create a functional double-stranded promoter. An RNA polymerase specific for the promoter sequence then binds to the functional promoter and transcribes multiple RNA transcripts complementary to the cDNA and substantially identical to the target region sequence that was amplified from the initial target strand. The resulting amplified RNA can then cycle through the process again by binding the primer and serving as a template for further cDNA production, ultimately producing many amplicons from the initial target nucleic acid present in the sample. Some embodiments of the single-primer transcription associated amplification method do not include the binding molecule and, therefore, the cDNA product made from the primer has an indeterminate 3' end, but the amplification steps proceed substantially as described above for all other steps.

Suitable amplification conditions can be readily determined by a skilled artisan in view of the present disclosure. "Amplification conditions" refer to conditions which permit nucleic acid amplification according to the present invention. Amplification conditions may, in some embodiments, be less stringent than "stringent hybridization conditions" as described herein. Oligos used in the amplification reactions of the present invention are specific for and hybridize to their intended targets under amplification conditions, but may or may not hybridize under more stringent hybridization conditions. On the other hand, detection probes of the present invention hybridize under stringent hybridization conditions. While the Examples section infra provides preferred amplification conditions for amplifying target nucleic acid sequences according to the present invention, other acceptable conditions to carry out nucleic acid amplifications according to the present invention could be easily ascertained by someone having ordinary skill in the art depending on the particular method of amplification employed.

The amplification methods of the invention, in certain embodiments, also preferably employ the use of one or more other types of oligos that are effective for improving the sensitivity, selectivity, efficiency, etc., of the amplification reaction. These may include, for example, terminating oligonucleotides, extender or helper oligonucleotides, and the like.

Target Capture

In certain embodiments, it may be preferred to purify or enrich a target nucleic acid from a sample prior to amplification, for example using a target capture approach. "Target capture" (TC) refers generally to capturing a target polynucleotide onto a solid support, such as magnetically attractable particles, wherein the solid support retains the target polynucleotide during one or more washing steps of the target polynucleotide purification procedure. In this way, the target polynucleotide is substantially purified prior to a subsequent nucleic acid amplification step. Numerous target capture methods are known and suitable for use in conjunction with the methods described herein.

A "capture oligonucleotide", "capture oligo", or "capture probe" refers to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (i.e., target-specific portion) and an immobilized probe-binding region, usually on the same oligomer, although the two regions may be present on two different oligomers joined together by one or more linkers.

An "immobilized oligo", "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. Any support may be used, e.g., matrices or particles free in solution, which may be made of any of a variety of materials, e.g., nylon, nitrocellulose, glass, polyacrylate, mixed polymers, polystyrene, silane polypropylene, or metal. Illustrative examples use a support that is magnetically attractable particles, e.g., monodisperse paramagnetic beads (uniform size.+−.5%) to which an immobilized probe is joined directly (e.g., via covalent linkage, chelation, or ionic interaction) or indirectly (e.g., via a linker), where the joining is stable during nucleic acid hybridization conditions.

For example, one illustrative approach, as described in U.S. Patent Application Publication No 20060068417, uses at least one capture probe oligonucleotide that contains a target-complementary region and a member of a specific binding pair that attaches the target nucleic acid to an immobilized probe on a capture support, thus forming a capture hybrid that is separated from other sample components before the target nucleic acid is released from the capture support.

In another illustrative method, Weisburg et al., in U.S. Pat. No. 6,110,678, describe a method for capturing a target polynucleotide in a sample onto a solid support, such as magnetically attractable particles, with an attached immobilized probe by using a capture probe and two different hybridization conditions, which preferably differ in temperature only. The two hybridization conditions control the order of hybridization, where the first hybridization conditions allow hybridization of the capture probe to the target polynucleotide, and the second hybridization conditions allow hybridization of the capture probe to the immobilized probe. The method may be used to detect the presence of a target polynucleotide in a sample by detecting the captured target polynucleotide or amplified target polynucleotide.

Another illustrative target capture technique (U.S. Pat. No. 4,486,539) involves a hybridization sandwich technique for capturing and for detecting the presence of a target polynucleotide. The technique involves the capture of the target polynucleotide by a probe bound to a solid support and hybridization of a detection probe to the captured target polynucleotide. Detection probes not hybridized to the target polynucleotide are readily washed away from the solid support. Thus, remaining label is associated with the target polynucleotide initially present in the sample.

Another illustrative target capture technique (U.S. Pat. No. 4,751,177) involves a method that uses a mediator polynucleotide that hybridizes to both a target polynucleotide and to a polynucleotide fixed on a solid support. The mediator polynucleotide joins the target polynucleotide to the solid support to produce a bound target. A labeled probe can be hybridized to the bound target and unbound labeled pro can be washed away from the solid support.

Yet another illustrative target capture technique is described in U.S. Pat. Nos. 4,894,324 and 5,288,609, which describe a method for detecting a target polynucleotide. The method utilizes two single-stranded polynucleotide segments complementary to the same or opposite strands of the target and results in the formation of a double hybrid with the target polynucleotide. In one embodiment, the hybrid is captured onto a support.

In another illustrative target capture technique, EP Pat. Pub. No. 0 370 694, methods and kits for detecting nucleic acids use oligonucleotide primers labeled with specific binding partners to immobilize primers and primer extension products. The label specifically complexes with its receptor which is bound to a solid support.

The above capture techniques are illustrative only, and not limiting. Indeed, essentially any technique available to the skilled artisan may be used provided it is effective for purifying a target nucleic acid sequence of interest prior to amplification.

Nucleic Acid Detection

Essentially any labeling and/or detection system that can be used for monitoring specific nucleic acid hybridization can be used in conjunction with the present invention to detect *Pseudomonas aeruginosa* amplicons. Many such systems are known and available to the skilled artisan, illustrative examples of which are briefly discussed below.

Detection systems typically employ a detection oligo of one type or another in order to facilitate detection of the target nucleic acid of interest. A "detection oligo" or "detection probe" refers to a nucleic acid oligo that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). A probe's target sequence generally refers to the specific sequence within a larger sequence which the probe hybridizes specifically. A detection probe may include target-specific sequences and other sequences or structures that contribute to the probe's three-dimensional structure, depending on whether the target sequence is present (e.g., U.S. Pat. Nos. 5,118,801, 5,312,728, 6,835,542, and 6,849,412).

Any of a number of well known labeling systems may be used to facilitate detection. A "label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent or chemiluminescent compound), and fluorescent compound. Preferred embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 6,004,745, 5,656,207 and 5,658,737). Preferred homogeneous detectable labels include chemiluminescent compounds, more preferably acridinium ester ("AE") compounds, such as standard AE or AE derivatives which are well known (U.S. Pat. Nos. 5,656,207, 5,658,737, and 5,948,899). Methods of synthesizing labels, attaching labels to nucleic acid, and detecting signals from labels are well known (e.g., Sambrook et al., Molecular Cloning, A Laboratory Manual, 2nd ed. (Cold Spring Harbor Laboratory Press, Cold Spring Harbor, N.Y., 1989) at Chapter. 10, and U.S. Pat. Nos. 6,414,152, 5,185,439, 5,658,737, 5,656,207, 5,547,842, 5,639,604, 4,581,333, and 5,731,148). Preferred methods of linking an AE compound to a nucleic acid are known (e.g., U.S. Pat. Nos. 5,585,481 and 5,639,604, see column 10, line 6 to column 11, line 3, and Example 8). Preferred AE labeling positions are a probe's central region and near a region of A/T base pairs, at a probe's 3' or 5' terminus, or at or near a mismatch site with a known sequence that is the probe should not detect compared to the desired target sequence.

In a preferred embodiment, oligos exhibiting at least some degree of self-complementarity are desirable to facilitate detection of probe:target duplexes in a test sample without first requiring the removal of unhybridized probe prior to detection. By way of example, structures referred to as "molecular torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions of the molecular torch, which may be fully or partially complementary, melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., a fluorescent/quencher pair) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference herein.

Another example of a self-complementary hybridization assay probe that may be used in conjunction with the invention is a structure commonly referred to as a "molecular beacon." Molecular beacons comprise nucleic acid molecules having a target complementary sequence, an affinity pair (or nucleic acid arms) that holds the probe in a closed conformation in the absence of a target nucleic acid sequence, and a label pair that interacts when the probe is in a closed conformation. Hybridization of the molecular beacon target complementary sequence to the target nucleic acid separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference herein. Molecular beacons useful for detecting specific nucleic acid sequences may be created by appending to either end of one of the probe sequences disclosed herein, a first nucleic acid arm comprising a fluorophore and a second nucleic acid arm comprising a quencher moiety. In this configuration, the *Pseudomonas aeruginosa*-specific probe sequences disclosed herein serves as the target-complementary "loop" portion of the resulting molecular beacon.

Molecular beacons are preferably labeled with an interactive pair of detectable labels. Preferred detectable labels interact with each other by FRET or non-FRET energy transfer mechanisms. Fluorescence resonance energy transfer (FRET) involves the radiationless transmission of energy quanta from the site of absorption to the site of its utilization in the molecule or system of molecules by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close such that energy emitted by one label can be received or absorbed by the second label, whether by a FRET or non-FRET mechanism, the two labels are said to be in an "energy transfer relationship." This is the case, for example, when a molecular beacon is maintained in the closed state by formation of a stem duplex and fluorescent emission from a fluorophore attached to one arm of the molecular beacon is quenched by a quencher moiety on the other arm.

Illustrative label moieties for the molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same molecular beacon is in the open state and is stimulated by an appropriate frequency of light, the fluorophore and the quencher moieties are sufficiently separated from each other such that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluorescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2, and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the Black Hole Quencher moieties, which are available from Biosearch Technologies, Inc. (Novato, Calif.).

Synthetic techniques and methods of attaching labels to nucleic acids and detecting labels are well known in the art (see, e.g., Sambrook et al., Molecular Cloning: A Laboratory Manual, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. Nos. 5,185,439 and 6,004,745; Kourilsky et al., U.S. Pat. No. 4,581,333; and, Becker et al., U.S. Pat. No. 5,731,148).

Preferred *Pseudomonas Aeruginosa* Oligos and Oligo Sets

As described herein, preferred sites for amplifying and detecting *Pseudomonas aeruginosa* nucleic acids according to the present invention have been found to reside in the 800 region of *Pseudomonas aeruginosa* 23s rRNA. Moreover, particularly preferred oligonucleotides and oligonucleotide sets within this region have been identified for amplifying *Pseudomonas aeruginosa* 23s with improved sensitivity, selectivity and specificity. It will be understood that the oligonucleotides of the invention are capable of hybridizing to a *Pseudomonas aeruginosa* target sequence with high specificity and, as a result, are capable of participating in a nucleic acid amplification reaction that can be used to detect the presence and/or levels of *Pseudomonas aeruginosa* in a sample and distinguish it from the presence of other pseudomonads.

For example, in one embodiment, the amplification oligonucleotides of the invention comprise a first oligonucleotide and a second oligonucleotide, wherein the first and second oligonucleotides target the 800 region of the *Pseudomonas aeruginosa* 23s rRNA with a high degree of specificity. Of course, it will be understood, when discussing the amplification oligonucleotides of the invention, that the first and second oligonucleotides used in an amplification reaction have specificity for opposite strands of the target nucleic acid sequence to be amplified.

In a particular embodiment, the amplification oligonucleotides of the invention comprise a first oligonucleotide and a second oligonucleotide, wherein the first oligonucleotide targets the complement of a sequence in a region of *Pseudomonas aeruginosa* 23s rRNA corresponding to bases from about 725-825 of *E. coli* 23s rRNA, and the second oligonucleotide targets a sequence in a region of *Pseudomonas aeruginosa* 23s rRNA corresponding to bases from about 845-950 of *E. coli* 23s rRNA.

The amplification oligonucleotides of the invention are particularly effective for amplifying a target nucleic acid sequence of *Pseudomonas aeruginosa* in a transcription-based amplification reaction, preferably a transcription-mediated amplification (TMA) reaction.

Certain amplification oligonucleotides of the invention are used in a transcription-mediated amplification reaction and comprise a T7 provider oligonucleotide and a non-T7 primer oligonucleotide, wherein the T7 provider targets the complement of a sequence in a region of *Pseudomonas aeruginosa* 23s rRNA corresponding to bases from about 725-825 of *E. coli* 23s rRNA, and the non-T7 primer targets a sequence in a region of *Pseudomonas aeruginosa* 23s rRNA corresponding to bases from about 845-950 of *E. coli* 23s rRNA.

Certain more specific amplification oligonucleotides of the invention comprise a T7 provider oligonucleotide and a non-T7 primer oligonucleotide, wherein the T7 provider targets the complement of a sequence in a region of *Pseudomonas aeruginosa* 23s rRNA corresponding to bases from about 725-775 of *E. coli* 23s rRNA, and the non-T7 primer targets a sequence in a region of the *Pseudomonas aeruginosa* 23s rRNA corresponding to bases from about 900-950 of *E. coli* 23s rRNA.

Other specific amplification oligonucleotides of the invention comprise a T7 provider oligonucleotide and a non-T7 primer oligonucleotide, wherein the T7 provider targets the complement of a sequence in a region of *Pseudomonas aeruginosa* 23s rRNA corresponding to bases from about 739-766 of *E. coli* 23s rRNA, and the non-T7 primer targets *Pseudomonas aeruginosa* 23s rRNA corresponding to bases from about 918-943 of *E. coli* 23s rRNA.

In a specific and preferred embodiment, the amplification oligonucleotides of the invention comprise a T7 provider oligonucleotide and a non-T7 primer oligonucleotide, wherein the T7 provider is selected from SEQ ID NO:2, SEQ ID NO:1, SEQ ID NO:11 or SEQ ID NO:14, and the non-T7 primer is selected from SEQ ID NO:22, SEQ ID NO:24, SEQ ID NO:19 or SEQ ID NO:15.

In another preferred embodiment, the amplification oligonucleotides of the invention comprise a T7 provider oligonucleotide and a non-T7 primer oligonucleotide, wherein the T7 provider is SEQ ID NO:2 and the non-T7 primer is SEQ ID NO:24.

It will be understood that in addition to the particular T7 provider oligonucleotides and non-T7 primer oligonucleotides used in the amplification reaction, additional oligonucleotides will also generally be employed in conjunction with the amplification reaction. For example, in certain embodiments, the amplification reactions will also employ the use of one or more of a detection oligonucleotide (e.g., a torch oligonucleotide), a blocker oligonucleotide and/or an extend oligonucleotide.

Table 1 below presents specific examples of T7 provider oligonucleotides, non-T7 primer oligonucleotides, and other ancillary oligonucleotides (e.g., blocker oligonucleotides, extend oligonucleotides and torch oligonucleotides) that have been identified by the present invention as having particularly preferred features.

TABLE 1

Examples of Preferred Oligos

| Oligo Description | Oligo ID | Sequence 5'-3' |
|---|---|---|
| T7 provider | SEQ ID NO: 2 | AATTTAATACGACTCACTATAGGGAGA CGTTGAAAAGGTAGGGGATGACTTGTGG X |
| | SEQ ID NO: 1 | AATTTAATACGACTCACTATAGGGAGA GAACCCACTCCCGTTGAAAAGGTAG G X |
| | SEQ ID NO: 11 | AATTTAATACGACTCACTATAGGGAGA CTCGGAGATAGCTGGTTCTCCTCGAAAGC X |
| | SEQ ID NO: 14 | AATTTAATACGACTCACTATAGGGAGA GCTGGTTCTCCTCGAAAGC X |
| Non-T7 primer | SEQ ID NO: 22 | ccauGCTCGGCACTTCTGGGTATTCG |
| | SEQ ID NO: 24 | GTGTGTCTCCCATGCTCGGCACTTCTG |
| | SEQ ID NO: 19 | cgguTTGGTAAGTCGGGATGACCC |
| | SEQ ID NO: 15 | ccuaGCCGAAACAGTTGCTCTACCC |

TABLE 1-continued

Examples of Preferred Oligos

| Oligo Description | Oligo ID | Sequence 5'-3' |
| --- | --- | --- |
| Torch | SEQ ID NO: 51 | cccagagugauacaugcuggg |
|  | SEQ ID NO: 54 | cccagagugauaccuggg |
|  | SEQ ID NO: 50 | gccucagagugauacaugaggc |
|  | SEQ ID NO: 56 | cccagagugauacaugagcuggg |
| Blocker | SEQ ID NO: 29 | caacgggaguggguucggu X |
|  | SEQ ID NO: 26 | gguucgguccuccagucag X |
|  | SEQ ID NO: 40 | ccgagcuugauuagccuuucacuccg X |
|  | SEQ ID NO: 42 | ccagcuaucuccgagcuugauuagc X |
| Extend Oligo | SEQ ID NO: 43 | GGATGACTTGTGGATCGGAGTGAAAGG X |
|  | SEQ ID NO: 44 | ATCGGAGTGAAAGGCTAATCAAGCTCG X |

Lower case 2'-O--methyl RNA
X is a blocking moiety (e.g., reverse (3'-5') C blocked)

In addition, Table 2 below identifies a particularly preferred oligonucleotide set for use in the compositions, kits and methods of the present invention, which comprises the T7 provider oligonucleotide SEQ ID NO:2 and the non-T7 primer oligonucleotide, SEQ ID NO:24, and optionally further comprises the blocker oligonucleotide SEQ ID NO:29, the torch oligonucleotide SEQ ID NO:54, the extend oligonucleotide SEQ ID NO:44, the target capture oligonucleotide SEQ ID NO:69 and, optionally, the target capture helper oligonucleotide SEQ ID NO:73.

TABLE 2

Example of Preferred Oligo Set

| Oligo Description | Oligo ID | Sequence 5'-3' |
| --- | --- | --- |
| Torch | SEQ ID NO: 54 | cccagagugauaccuggg |
| T7 provider | SEQ ID NO: 2 | AATTTAATACGACTCACTATAGGGAGACGTTGAAAAGGTAGGGGATGACTTGTGG X |
| Blocker | SEQ ID NO: 29 | caacgggaguggguucggu X |
| Non-T7 Primer | SEQ ID NO: 24 | GTGTGTCTCCCATGCTCGGCACTTCTG |
| Extend Oligo | SEQ ID NO: 44 | ATCGGAGTGAAAGGCTAATCAAGCTCG X |
| Target Capture Oligo | SEQ ID NO: 68 | gcuccucuaccgcgucacuuacg-dT$_3$dA$_{30}$ |
| Target Capture Oligo Helper | SEQ ID NO: 73 | cucaacucaccuucacaggcuuacagaacX |

Lower case 2'-O--methyl RNA
X is a blocking moiety (e.g., reverse (3'-5') C blocked)

While specifically preferred amplification oligonucleotides derived from the 800 region have been identified according to the invention, which result in superior assay performance, it will be recognized that other oligonucleotides derived from the 800 region and having insubstantial modifications from those specifically described herein may also be used, provided the same or similar performance objectives are achieved. For example, oligonucleotides derived from the 800 region and useful in the amplification reactions according to the invention can have different lengths from those identified herein, provided it does not substantially affect amplification and/or detection procedures. These and other routine and insubstantial modifications to the preferred oligonucleotides of the invention can carried out using conventional techniques, and to the extent such modifications maintain one or more advantages provided herein they are considered within the spirit and scope of the present invention.

Preferred Compositions and Kits for Detecting *Pseudomonas Aeruginosa*

The present invention also embraces compositions, reaction mixtures and kits for performing polynucleotide amplification reactions for detecting the 800 region of the 23s rRNA of *Pseudomonas aeruginosa*. Exemplary kits include first and second amplification oligonucleotides that are complementary to opposite strands of the 800 region of the 23s rRNA of *Pseudomonas aeruginosa*. Certain preferred kits will contain oligonucleotides described herein for use in a transcription-associated amplification reaction, preferably a TMA reaction. In one preferred embodiment, a kit of the invention will comprise a T7 provider oligonucleotide as described herein, a non-T7 primer oligonucleotide as described herein, and optionally will further comprise one or more other ancillary oligonucleotides to facilitate amplification and/or detection, including one or more of a detection oligonucleotide, capture oligonucleotide, blocker oligonucleotide, and/or extend oligonucleotide, as described herein.

In certain embodiments, the present invention is drawn to compositions, reaction mixtures and kits comprising a first oligonucleotide and a second oligonucleotide, wherein the first and second oligonucleotides target the 800 region of the *Pseudomonas aeruginosa* 23s rRNA with high specificity. Of course, it will be understood, when discussing the amplification oligonucleotides of the invention that target certain residues within this 800 region, that the first and second oligonucleotides used in an amplification reaction are complementary to opposite strands of the target nucleic acid sequence to be amplified.

In a particular embodiment, the present invention is drawn to compositions, reaction mixtures and kits, for use in an amplification reaction, comprising a first oligonucleotide and a second oligonucleotide, wherein the first oligonucleotide targets the complement of a sequence in a region of *Pseudomonas aeruginosa* 23s rRNA corresponding to bases from about 725-825 of *E. coli* 23s rRNA, and the second oligonucleotide targets a sequence in a region of *Pseudomonas aeruginosa* 23s rRNA corresponding to bases from about 845-950 of *E. coli* 23s rRNA.

In another embodiment, the present invention is drawn to compositions, reaction mixtures and kits, for use in a transcription mediated amplification reaction, comprising a T7 provider oligonucleotide and a non-T7 primer oligonucleotide, wherein the T7 provider targets the complement of a sequence in a region of *Pseudomonas aeruginosa* 23s rRNA corresponding to bases from about 725-825 of *E. coli* 23s rRNA, and the non-T7 primer targets a sequence in a region of the *Pseudomonas aeruginosa* 23s rRNA corresponding to bases from about 845-950 of *E. coli* 23s rRNA.

In a more particular embodiment, the present invention is drawn to compositions, reaction mixtures and kits, for use in a transcription mediated amplification reaction, comprising a T7 provider oligonucleotide and a non-T7 primer oligonucleotide, wherein the T7 provider targets the complement of a sequence in a region of *Pseudomonas aeruginosa* 23s rRNA corresponding to bases from about 725-775 of *E. coli* 23s rRNA, and the non-T7 primer targets a sequence in a region of *Pseudomonas aeruginosa* 23s rRNA corresponding to bases from about 900-950 of *E. coli* 23s rRNA.

In a more specific embodiment, the present invention is drawn to compositions, reaction mixtures and kits, for use in a transcription mediated amplification reaction, comprising a T7 provider oligonucleotide and a non-T7 primer oligonucleotide, wherein the T7 provider targets the complement of a sequence in a region of the *Pseudomonas aeruginosa* 23s rRNA corresponding to bases from about 739-766 of *E. coli* 23s rRNA, and the non-T7 primer targets a sequence in a region of the *Pseudomonas aeruginosa* 23s rRNA corresponding to bases from about 918-943 of *E. coli* 23s rRNA.

In one preferred embodiment, the present invention is drawn to compositions, reaction mixtures and kits, for use in a transcription mediated amplification reaction, comprising at least a T7 provider oligonucleotide and a non-T7 primer oligonucleotide, wherein the T7 provider is selected from SEQ ID NO:2, SEQ ID NO:1, SEQ ID NO:11 or SEQ ID NO:14, and the non-T7 primer is selected from SEQ ID NO:22, SEQ ID NO:24, SEQ ID NO:19 or SEQ ID NO:15.

In another preferred embodiment, the present invention is drawn to compositions, reaction mixtures and kits, for use in a transcription mediated amplification reaction, comprising at least a T7 provider oligonucleotide and a non-T7 primer oligonucleotide, wherein the T7 provider is SEQ ID NO:2 and the non-T7 primer is SEQ ID NO:24.

It will be understood that in addition to the particular T7 provider oligonucleotides and non-T7 primer oligonucleotides used in the amplification reaction, additional ancillary oligonucleotides will also generally be employed in conjunction with the amplification reaction. For example, in certain embodiments, the compositions, reaction mixtures and kits of the invention will also further comprise one or more of a target capture oligonucleotide, torch oligonucleotide, blocker oligonucleotide and/or extend oligonucleotide.

For example, in one embodiment, the compositions, reaction mixtures and/or kits of the invention, in addition to the T7 provider oligonucleotide and non-T7 primer oligonucleotide, will further comprise a torch oligonucleotide. In a particular embodiment, the torch oligonucleotide is selected from SEQ ID NO:51, SEQ ID NO:54, SEQ ID NO:50 or SEQ ID NO:56. In one preferred embodiment, the torch oligonucleotide is SEQ ID NO:54.

In another embodiment, the compositions, reaction mixtures and/or kits of the invention, in addition to the T7 provider oligonucleotide and non-T7 primer oligonucleotide, will further comprise an extend oligonucleotide. In a particular embodiment, the extend oligonucleotide is selected from SEQ ID NO:43 or SEQ ID NO: 44.

In another embodiment, the compositions, reaction mixtures and/or kits of the invention, in addition to the T7 provider oligonucleotide and non-T7 primer oligonucleotide, will further comprise a blocker oligonucleotide. In a particular embodiment, the blocker oligonucleotide is selected from SEQ ID NO:29, SEQ ID NO:26, SEQ ID NO:40 or SEQ ID NO:42.

In another embodiment, the compositions, reaction mixtures and/or kits of the invention, in addition to the T7 provider oligonucleotide and non-T7 primer oligonucleotide, will further comprise a target capture oligonucleotide and, optionally, a target capture helper oligonucleotide. In a particular embodiment, the target capture oligonucleotide SEQ ID NO:69 and the target capture helper oligonucleotide is SEQ ID NO:73.

In a particularly preferred embodiment, the compositions, reaction mixtures and/or kits of the invention comprise the T7 provider oligonucleotide, SEQ ID NO:2 and the non-T7 primer oligonucleotide, SEQ ID NO:24; and optionally further comprises the blocker oligonucleotide SEQ ID NO:29, the torch oligonucleotide SEQ ID NO:54, the extend oligonucleotide SEQ ID NO:44, the target capture oligonucleotide SEQ ID NO:69, and optionally, the target capture helper oligonucleotide SEQ ID NO:73.

The general principles of the present invention may be more fully appreciated by reference to the following non-limiting Examples.

EXAMPLES

Examples are provided below illustrating certain aspects and embodiments of the invention. The examples below are believed to accurately reflect the details of experiments actually performed, however, it is possible that some minor discrepancies may exist between the work actually performed and the experimental details set forth below which do not affect the conclusions of these experiments or the ability of skilled artisans to practice them. Skilled artisans will appreciate that these examples are not intended to limit the invention to the specific embodiments described therein. Additionally, those skilled in the art, using the techniques, materials and methods described herein, could easily devise and optimize alternative amplification systems for carrying out these and related methods while still being within the spirit and scope of the present invention.

Unless otherwise indicated, oligonucleotides and modified oligonucleotides in the following examples were synthesized using standard phosphoramidite chemistry, various methods of which are well known in the art. See e.g., Carruthers, et al., 154 Methods in Enzymology, 287 (1987), the contents of which are hereby incorporated by reference herein. Unless otherwise stated herein, modified nucleotides were 2'-O-methyl ribonucleotides, which were used in the synthesis as their phosphoramidite analogs. For blocked oligonucleotides used in single-primer amplification (Becker et al., US2006/0046265, hereby incorporated by reference herein), the 3'-terminal blocking moiety consisted of a "reversed C" 3'-to-3' linkage prepared using 3'-dimethyltrityl-N-benzoyl-2'-deoxycytidine, 5'-succinoyl-long chain alkylamino-CPG (Glen Research Corporation, Cat. No. 20-0102-01). Molecular torches (see Becker et al., U.S. Pat. No. 6,849,412, hereby incorporated by reference herein) were prepared using a C9 non-nucleotide linker joining region, 5'-fluorescein ("F") fluorophore and 3'-dabsyl ("D") quencher moieties attached to the oligonucleotide by standard methods.

As set forth in the examples below, analyses of a wide variety of amplification reagents and conditions has led to the development of a highly sensitive and selective amplification process for the species-specific detection of *Pseudomonas aeruginosa*.

Example 1

Description of Illustrative Assay Reagents and Protocols

The following example describes typical assay reagents, protocols, conditions and the like used in the TMA experiments described herein. Unless specified to the contrary, reagent preparation, equipment preparation and assay protocols were performed essentially as set forth below.

A. Reagents and Samples

1. Amplification Reagent. The "Amplification Reagent" or "Amp Reagent" comprised approximate concentrations of the following components: 0.5 mM dATP, 0.5 mM dCTP, 0.5 mM dGTP, 0.5 mM dTTP, 10 mM ATP, 2 mM CTP, 2 mM GTP, 12.7 mM UTP, 30 mM $MgCl_2$, and 33 mM KCl in 50 mM HEPES buffer at pH 7.7. Primers and other oligonucleotides were added to the Amp Reagent.

2. Enzyme Reagent. The "Enzyme Reagent" comprised approximate concentrations of the following components: 1180 RTU/μL Moloney murine leukemia virus ("MMLV") reverse transcriptase ("RT") and 260 PU/μL T7 RNA polymerase in 75 mM HEPES buffer containing 120 mM KCl, 10% TRITON® X-100, 160 mM N-acetyl-L-cysteine, and 1 mM EDTA at pH 7.0, where one RTU of RT activity incorporates 1 nmol of dT into a substrate in 20 minutes at 37° C. and one PU of T7 RNA polymerase activity produces 5 fmol of RNA transcript in 20 minutes at 37° C.

3. Wash Solution. The "Wash Solution" comprised 0.1% (w/v) sodium dodecyl sulfate, 150 mM NaCl and 1 mM EDTA in 10 mM HEPES buffer at pH to 7.5.

4. Target Capture Reagent. The "Target Capture Reagent" (TCR) comprised approximate concentrations of the following components: 60 pmol/mL each of one or more capture probes having a $dT_3dA_{30}$ tail and an optional capture helper probe, 250 to 300 ug/mL paramagnetic oligo-$(dT)_{14}$ microparticles (Seradyn), 250 mM HEPES, 100 mM EDTA and 1.88 M LiCl at pH 6.5.

5. Lysis Reagent. The "Lysis Buffer" comprised 1% lithium lauryl sulfate in a buffer containing 100 mM tris, 2.5 mM succinic acid, 10 mM EDTA and 500 mM LiCl at pH 6.5.

6. Target rRNA Samples. rRNA samples were stored in water, 0.1% LiLS or Lysis Reagent prior to use in the experiments described herein.

B. Target Capture

A typical target capture procedure to purify and prepare nucleic acid samples for subsequent amplification is performed essentially as described below.

1. Combine 100 uL of test sample, 50 μL of the TCR containing target capture oligonucleotides and 1 mL Lysis Reagent. Incubate the mixture at 60° C. for 15 minutes 2. Capture and wash the TCR magnetic particles from the treated reaction mixture using the Wash Solution and a suitable magnetic particle washing and separation device (e.g., a magnetic separation rack, a GEN-PROBE® Target Capture System, Gen-Probe Cat. No. 5207, or a King-Fisher® magnetic particle processor system available from Thermo Labsystems).

3. After washing, the magnetic particles are resuspended in 100 μL of the Amplification Reagent.

C. Amplification and Detection of Target

The real-time TMA amplification reactions were performed essentially as follows. 30 μL of sample, amplification and detection oligonucleotides in the Amp Reagent or 30 μL of the resuspended particles in the Amp Reagent from the target capture procedure was incubated at 60° C. for 10 minutes. The temperature was then reduced and the reaction mixture was equilibrated to 42° C. 10 μL of Enzyme Reagent was added. The reaction mixture was mixed and incubated at 42° C. in a real-time detection system (e.g., Opticon™ or Chromo4™ detection systems available from Bio-Rad Laboratories, or a FluoDia® T70 instrument).

Example 2

Design and Initial Testing of *Pseudomonas Aeruginosa* (Pae) Oligo Sets

Amplication and detection oligonucleotides targeting two regions of *Pseudomonas aeruginosa* nucleic acid corresponding to from about 700 to 1000 ("800 region") and from about 1400 to 1600 ("1500 region") nucleotide base positions of *E. coli* 23s rRNA (Accession No. V00331) were designed and synthesized for evaluation.

TABLE 3

| | 800 Region oligos | |
|---|---|---|
| Use | SEQ ID NO: | Sequence (5'-3') |
| T7 Provider | 1 | AATTTAATACGACTCACTATAGGGAGA GAACCCACTCCCGTTGAAAAGGTAGG-X |

TABLE 3-continued

800 Region oligos

| Use | SEQ ID NO: | Sequence (5'-3') |
|---|---|---|
| T7 Provider | 2 | AATTTAATACGACTCACTATAGGGAGA CGTTGAAAAGGTAGGGGATGACTTGTGG-X |
| T7 Provider | 3 | AATTTAATACGACTCACTATAGGGAGA GGATGACTTGTGGATCGGAGTGAAAGGCTAATC-X |
| T7 Provider | 4 | AATTTAATACGACTCACTATAGGGAGA GTGGATCGGAGTGAAAGGCTAATCAAGCTC-X |
| T7 Provider | 5 | AATTTAATACGACTCACTATAGGGAGA TCGGAGTGAAAGGCTAATCAAGCTCGGAGATAG-X |
| T7 Provider | 6 | AATTTAATACGACTCACTATAGGGAGA TCGGAGTGAAAGGCTAATCAAGCTCGGAG-X |
| T7 Provider | 7 | AATTTAATACGACTCACTATAGGGAGA GAGTGAAAGGCTAATCAAGCTCGGAGATAGCTG-X |
| T7 Provider | 8 | AATTTAATACGACTCACTATAGGGAGA GGCTAATCAAGCTCGGAGATAGCTGGTTC-X |
| T7 Provider | 9 | AATTTAATACGACTCACTATAGGGAGA GGCTAATCAAGCTCGGAGATAGCTGGTTCTCC-X |
| T7 Provider | 10 | AATTTAATACGACTCACTATAGGGAGA ATCAAGCTCGGAGATAGCTGGTTCTCCTCGAA-X |
| T7 Provider | 11 | AATTTAATACGACTCACTATAGGGAGA CTCGGAGATAGCTGGTTCTCCTCGAAAGC-X |
| T7 Provider | 12 | AATTTAATACGACTCACTATAGGGAGA GGAGATAGCTGGTTCTCCTCGAAAGCTATTTA-X |
| T7 Provider | 13 | AATTTAATACGACTCACTATAGGGAGA AGCTGGTTCTCCTCGAAAGCTATTTAGGTAG-X |
| T7 Provider | 14 | AATTTAATACGACTCACTATAGGGAGA GCTGGTTCTCCTCGAAAGC-X |
| Primer | 15 | ccuaGCCGAAACAGTTGCTCTACCC |
| Primer | 16 | gucgGGATGACCCCCTAGCCGAAACAGTTG |
| Primer | 17 | gucgGGATGACCCCCTAGCCGAAACAG |
| Primer | 18 | gguaAGTCGGGATGACCCCCTAGCCGAAA |
| Primer | 19 | cgguTTGGTAAGTCGGGATGACCC |
| Primer | 20 | guauTCGGAGTTTGCATCGGTTTGGTA |
| Primer | 21 | CTTCTGGGTATTCGGAGTTTGCATCGGTTTG |
| Primer | 22 | ccauGCTCGGCACTTCTGGGTATTCG |
| Primer | 23 | augcTCGGCACTTCTGGGTATTCGGAG |
| Primer | 24 | GTGTGTCTCCCATGCTCGGCACTTCTG |
| Blocker | 25 | cgguccuccagucaguuuac-X |
| Blocker | 26 | gguucgguccuccagucag-X |
| Blocker | 27 | gaguggguucgguccuccag-X |
| Blocker | 28 | gggaguggguucgguccucc-X |
| Blocker | 29 | caacgggaguggguucggu-X |
| Blocker | 30 | cuuuucaacgggaguggguuc-X |
| Blocker | 31 | cauccccuaccuuuucaacgggagu-X |
| Blocker | 32 | cuaccuuuucaacgggagug-X |

TABLE 3-continued

800 Region oligos

| Use | SEQ ID NO: | Sequence (5'-3') |
|---|---|---|
| Blocker | 33 | uccacaagucaucccuaccuuuuc-X |
| Blocker | 34 | uccgauccacaagucaucccuacc-X |
| Blocker | 35 | cuccgauccacaagucaucccua-X |
| Blocker | 36 | cacuccgauccacaagucauccccu-X |
| Blocker | 37 | ucacuccgauccacaagucaucc-X |
| Blocker | 38 | uagccuuucacuccgauccacaagu-X |
| Blocker | 39 | cuugauuagccuuucacuccgaucc-X |
| Blocker | 40 | ccgagcuugauuagccuuucacuccg-X |
| Blocker | 41 | ucuccgagcuugauuagccuuucac-X |
| Blocker | 42 | ccagcuaucuccgagcuugauuagc-X |
| Extend oligo | 43 | GGATGACTTGTGGATCGGAGTGAAAGG-X |
| Extend oligo | 44 | ATCGGAGTGAAAGGCTAATCAAGCTCG-X |
| Extend oligo | 45 | CTGGTTCTCCTCGAAAGCTATTTAG-X |
| Torch | 46 | ccgagugauacaugaggcgcucgg |
| Torch | 47 | cccagagugauacaugaggcgcuggg |
| Torch | 48 | cccagagugauacaugaggcgcuggg |
| Torch | 49 | ccagagugauacaugaggcucugg |
| Torch | 50 | gccucagagugauacaugaggc |
| Torch | 51 | cccagagugauacaugcuggg |
| Torch | 52 | cccagagugauacaucuggg |
| Torch | 53 | cccagagugauacacuggg |
| Torch | 54 | cccagagugauaccuggg |
| Torch | 55 | cccagagugauacuggg |
| Torch | 56 | cccagagugauacaugagcuggg |
| Torch | 57 | cuacccccagagagauggguag |

TABLE 4

1500 Region Oligos

| Use | SEQ ID NO: | Sequence (5'-3') |
|---|---|---|
| Blocker | 58 | cacccacggccaagcgg-X |
| Blocker | 59 | ggauuuaccuaagauuucag-X |
| T7 Provider | 60 | AATTTAATACGACTCACTATAGGGAGA GGGTGGCCAAGTTTAAGGTGGTAGGC-X |
| T7 Provider | 61 | AATTTAATACGACTCACTATAGGGAGA GGTAAATCCGGGGTTTCAAGGCCG-X |
| Torch | 62 | cgacgacucgucaucacgucg |
| Primer | 63 | ggaaGCATGGCATCAAGCAC |
| Primer | 64 | ccugGTTACCTGAAGCTTAGAAGCTTTTCTTGG |

The 23S 1500 region designs were tested with results presented below in Cycle Time which is proportional to Ttime. Four combinations of oligos were tested with oligo set number two being the best candidate based on the curve shape (not shown) and earliest Cycle Time at 1E+06 copies of Pae rRNA.

TABLE 5

Summary of Oligo Screening for Pae 23S 1500 Region

| Set | Description | SEQ ID NO: | Cycle Time @ 0 copies RNA | Cycle Time @ 1E+06 copies RNA | Comments |
|---|---|---|---|---|---|
| 1) | T7 provider | 60 | 62.5 | 25.2 | Low amplification @ both copy levels |
|  | Blocker | 58 | None | 52.1 |  |
|  | Non-T7 primer | 63 | 66.5 | 54.9 |  |
|  | Torch | 62 | 46.6 | 53.7 |  |
| 2) | T7 provider | 60 | 47.7 | 32.5 | Best set even with contamination of reagents |
|  | Blocker | 58 | 49.4 | 20.9 |  |
|  | Non-T7 primer | 64 | 52.2 | 32.8 |  |
|  | Torch | 62 | 52.4 | 33.9 |  |
| 3) | T7 provider | 61 | None | 55.8 | Low amplification @ both copy levels |
|  | Blocker | 59 | None | 57.1 |  |
|  | Non-T7 primer | 63 | None | 53.1 |  |
|  | Torch | 62 | 25.6 | 56.7 |  |
| 4) | T7 provider | 61 | 67.7 | 46.0 | Second best set even with contamination of reagents |
|  | Blocker | 59 | 57.8 | 39.8 |  |
|  | Non-T7 primer | 64 | 26.6 | 40.5 |  |
|  | Torch | 62 | 7.4 | 41.9 |  |

Several optimization experiments with the 1500 region oligo set two were performed varying the concentrations of the oligos (results not shown). However, simultaneous testing with the long amplicon oligo set(s) in the 800 region showed a reduction in the level of background with the contaminated reagents. Accordingly, the 800 region of the 23S rRNA was selected as the preferred region for further optimization based upon the finding that T7 providers and non-T7 primers for this region displayed the highest signals and lowest background in a real-time single primer TMA assay, relative to the large number of other oligo sets tested. Screening of oligos in a real-time TMA assay was performed, and different torches and blockers were also analyzed. The criteria for selecting the best oligo sets included having the lowest background and the highest signal at 10e3 copies of *Pseudomonas aeruginosa* rRNA.

Three initial preferred oligo sets were selected from this analysis, including blockers and torches, and these sets are referred to as the standard short amplicon sets S1 and F11, and the long amplicon set LA2 (Table 6 below). Although each of the three sets performed well, the LA2 oligo set demonstrated no background and the best sensitivity. In addition, the LA2 oligo set was unusual as the amplicon produced, at about 196 bases in length, is longer than typical shorter amplicons (86-110 nucleotide bases) of F11 and S1.

TABLE 6

Summary Table of Initial 800 Region Oligos Sets Tested

| Oligo Set | Description | Oligo ID |
|---|---|---|
| S1 | T7 provider | SEQ ID NO: 11 |
|  | Blocker | SEQ ID NO: 40 |
|  | Torch | SEQ ID NO: 56 |
|  | Non-T7 primer | SEQ ID NO: 19 |

TABLE 6-continued

Summary Table of Initial 800 Region Oligos Sets Tested

| Oligo Set | Description | Oligo ID |
|---|---|---|
| F11 | T7 provider | SEQ ID NO: 14 |
|  | Blocker | SEQ ID NO: 42 |
|  | Torch | SEQ ID NO: 51 |
|  | Non-T7 primer | SEQ ID NO: 15 |
| LA2 | T7 provider | SEQ ID NO: 2 |
|  | Blocker | SEQ ID NO: 29 |
|  | Torch | SEQ ID NO: 50 |
|  | Non-T7 primer | SEQ ID NO: 22 |

Example 3

Further Identification of *Pseudomonas Aeruginosa* Oligo Sets

To further reduce background signals and improve specificity and sensitivity, a number of additional oligo sets were designed and tested. "Extend" oligos were also introduced in an effort to improve sensitivity. These experiments were performed without target capture.

Prior to the addition of the extend oligos and redesigns, one oligo set being tested (designated as the "standard" system) comprised a combination of the amplification oligos from the "LA2" oligo set and the torch from the "F11" oligo set (Table 7 below). This oligo set, however, exhibited specificity problems when challenged with *Pseudomonas putida*, had slightly elevated background signals, and had slow emergence times for *Pseudomonas aeruginosa* at $1\times10^3$ copies. Redesign and screening yielded three promising new oligo sets (Sets 1-3 below), which addressed these problems. All three oligo sets included the torch SEQ ID NO:54, which improved specificity and reduced background signals; extend oligos for improving assay sensitivity; and redesigned amplification oligos.

In addition, these new oligo sets were compared with another oligo set (Set 4 below) and the "standard LA" oligo set. All of the new oligo sets included torch SEQ ID NO:54, and they outperformed the "standard" oligo set.

Table 7 below summarizes the preferred oligo sets at this stage of the analysis. Table 7 below shows the sequences of preferred the T7 providers, non-T7 primers, extend oligos and blocker oligos.

TABLE 7

Summary of Certain Preferred Long Amplicon Oligo Sets

| Oligo Set | Description | Oligo |
|---|---|---|
| "Standard LA" Set (LA2 + F11 torch) | Torch | SEQ ID NO: 51 |
|  | T7 provider | SEQ ID NO: 2 |
|  | Blocker | SEQ ID NO: 29 |
|  | Non-T7 primer | SEQ ID NO: 22 |
| Set 1 | Torch | SEQ ID NO: 54 |
|  | T7 provider | SEQ ID NO: 2 |
|  | Blocker | SEQ ID NO: 25 |
|  | Extend Oligo | SEQ ID NO: 44 |
|  | Non-T7 primer | SEQ ID NO: 24 |
| Set 2 | Torch | SEQ ID NO: 54 |
|  | T7 provider | SEQ ID NO: 2 |
|  | Blocker | SEQ ID NO: 29 |
|  | Extend Oligo | SEQ ID NO: 44 |
|  | Non-T7 primer | SEQ ID NO: 22 |

TABLE 7-continued

Summary of Certain Preferred Long Amplicon Oligo Sets

| Oligo Set | Description | Oligo |
|---|---|---|
| Set 3 | Torch | SEQ ID NO: 54 |
| | T7 provider | SEQ ID NO: 1 |
| | Blocker | SEQ ID NO: 26 |
| | Extend Oligo | SEQ ID NO: 43 |
| | Non-T7 primer | SEQ ID NO: 24 |
| Set 4 | Torch | SEQ ID NO: 54 |
| | T7 provider | SEQ ID NO: 1 |
| | Blocker | SEQ ID NO: 26 |
| | Extend Oligo | SEQ ID NO: 43 |
| | Non-T7 primer | SEQ ID NO: 22 |

TABLE 8

Sequences for Preferred Oligos

| Description | Oligo | Sequence 5'-3' |
|---|---|---|
| Torch | SEQ ID NO: 51 | cccagagugauacaugcuggg |
| | SEQ ID NO: 54 | cccagagugauaccuggg |
| T7 provider | SEQ ID NO: 2 | AATTTAATACGACTCACTATAGGGAGA CGTT GAAAAGGTAGGGGATGACTTGTGG-X |
| | SEQ ID NO: 1 | AATTTAATACGACTCACTATAGGGAGA GAAC CCACTCCCGTTGAAAAGGTAGG X |
| Blocker | SEQ ID NO: 29 | caacgggaguggguucggu X |
| | SEQ ID NO: 26 | gguucgguccuccagucag X |
| Non-T7 primer | SEQ ID NO: 22 | ccauGCTCGGCACTTCTGGGTATTCG |
| | SEQ ID NO: 24 | GTGTGTCTCCCATGCTCGGCACTTCTG |
| Extend Oligo | SEQ ID NO: 43 | GGATGACTTGTGGATCGGAGTGAAAGG X |
| | SEQ ID NO: 44 | ATCGGAGTGAAAGGCTAATCAAGCTCG X |

Example 4

Further Characterization and Optimization of *Pseudomonas Aeruginosa* Oligo Sets Tables 9-13 below present and summarize representative data relating to the identification and optimization of certain preferred oligo sets of the present invention. The AveRange (RFU) and TTime (min) results from real-time TMA reactions are presented. Preferred oligos are determined from this analysis by the curve shape (not shown) and the results for the AveRange and TTime; the preferred oligo sets have the lowest relative fluorescence unit (RFU) and the longest TTime at the zero Pae rRNA copy level. High RFU values at the zero Pae rRNA copy level indicate possible contamination within the reagents.

Table 9 presents a summary of results for oligo set S1.

TABLE 9

Summary of results for oligo set S1

| Oligo Set | Copies Pae rRNA | AveRange (RFU) | TTime (min) | Comments |
|---|---|---|---|---|
| S1 | 0 | 0.341 | 20.6 | AveRange and TTime @ 0 copies Pae rRNA indicates contamination |
| | 1E+04 | 0.393 | 16.7 | |
| | 1E+05 | 0.297 | 14.8 | |
| | 1E+06 | 0.326 | 12.6 | |
| | 1E+07 | 0.417 | 10.8 | |
| | 1E+08 | 0.449 | 9.1 | |

Table 10 compares the S1 oligo set with the F11 oligo set and demonstrates for F11 the first reduction in RFU at the zero copy level. This finding was built upon for subsequent testing.

TABLE 10

Summary of results for oligo set S1 vs. F11

| Oligo Set | Copies Pae rRNA | AveRange (RFU) | TTime (min) | Comments |
|---|---|---|---|---|
| S1 | 0 | 0.745 | 18.9 | Contamination |
| | 1E+03 | 0.757 | 19.0 | |
| F11 pure | 0 | 0.503 | 33.8 | Contamination reduced |
| | 1E+03 | 0.727 | 29.2 | |
| F11 crude | 0 | 0.426 | 47.0 | Contamination reduced |
| | 1E+03 | 1.185 | 37.9 | |

The oligo set, LA2, as well as combinations of previously screened oligos, were tested and reductions in RFU values at the 0 copy level were also demonstrated (e.g., Table 11). The LA2 oligo set produces a much longer amplicon than for previous sets tested and the level of *Pseudomonas aeruginosa* contamination at the zero *P. aeruginosa* rRNA copy level was decreased even further (Table 11).

TABLE 11

Summary Table of LA2 & Combinations

| Oligo Set | Oligo Description (ID) | Copies Pae rRNA | Ave Range (RFU) | TTime (min) | Comments |
|---|---|---|---|---|---|
| Control (F11 amp + S1 torch) | T7 provider (SEQ ID NO: 14) | 0 | 0.389 | 14.9 | |
| | Blocker (SEQ ID NO: 42) | 1E+04 | 0.298 | 13.6 | |
| | Torch (SEQ ID NO: 56) | 1E+06 | 0.324 | 10.9 | |
| | Primer (SEQ ID NO: 15) | | | | |

TABLE 11-continued

Summary Table of LA2 & Combinations

| Oligo Set | Oligo Description (ID) | Copies Pae rRNA | Ave Range (RFU) | TTime (min) | Comments |
|---|---|---|---|---|---|
| Combo2 (LA2) | T7 provider (SEQ ID NO:2) | 0 | 0.183 | 34.6 | |
| | Blocker (SEQ ID NO: 29) | 1E+04 | 0.344 | 27.0 | |
| | Torch (SEQ ID NO: 50) | 1E+06 | 0.370 | 19.9 | |
| | Primer (SEQ ID NO: 22) | | | | |
| Combo3 | T7 provider (SEQ ID NO: 2) | 0 | 0.042 | 29.5 | Lower RFU & later TTime @ 0 copies |
| | Blocker (SEQ ID NO: 29) | 1E+04 | 0.312 | 23.7 | |
| | Torch (SEQ ID NO: 56) | 1E+06 | 0.308 | 17.9 | |
| | 1 Primer (SEQ ID NO: 5) | | | | |
| Combo4 | T7 provider (SEQ ID NO: 14) | 0 | 0.121 | 21.1 | |
| | Blocker (SEQ ID NO: 42) | 1E+04 | 0.305 | 17.9 | |
| | Torch (SEQ ID NO: 56) | 1E+06 | 0.378 | 13.9 | |
| | Primer (SEQ ID NO: 22) | | | | |
| Combo5 | T7 provider (SEQ ID NO: 2) | 0 | 0.088 | 28.7 | |
| | Blocker (SEQ ID NO: 29) | 1E+04 | 0.284 | 22.9 | |
| | Torch (SEQ ID NO: 50) | 1E+06 | 0.452 | 17.6 | |
| | Primer (SEQ ID NO: 15) | | | | |
| Combo6 | T7 provider (SEQ ID NO: 14) | 0 | 0.476 | 19.8 | |
| | Blocker (SEQ ID NO: 42) | 1E+04 | 0.350 | 17.5 | |
| | Torch (SEQ ID NO: 50) | 1E+06 | 0.422 | 13.5 | |
| | Primer (SEQ ID NO: 22) | | | | |
| Combo7 | T7 provider (SEQ ID NO: 14) | 0 | 0.567 | 14.2 | |
| | Blocker (SEQ ID NO: 42) | 1E+04 | 0.352 | 12.8 | |
| | Torch 9 SEQ ID NO: 50) | 1E+06 | 0.450 | 10.1 | |
| | Primer (SEQ ID NO: 15) | | | | |
| Combo8 | T7 provider (SEQ ID NO: 2) | 0 | 0.014 | 39.1 | Lowest RFU & latest TTime @ 0 copies |
| | Blocker (SEQ ID NO: 29) | 1E+04 | 0.211 | 28.4 | |
| | Torch (SEQ ID NO: 56) | 1E+06 | 0.302 | 22.0 | |
| | Primer (SEQ ID NO: 22) | | | | |

In addition, various torches were tested with the LA2 oligo set and the results are set forth in Table 12.

TABLE 12

Summary Table for various Non-T7 primer and Torch combinations

| Oligo Set | Oligo Description (ID) | Copies Pae rRNA | Ave Range (RFU) | TTime (min) | Comments |
|---|---|---|---|---|---|
| LA1 | T7 provider (SEQ ID NO: 2) | 0 | 0.090 | 22.2 | |
| | Blocker (SEQ ID NO: 29) | 1E+02 | 0.112 | 20.3 | |
| | Torch (SEQ ID NO: 50) | 1E+03 | 0.260 | 21.0 | |
| | Non-T7 primer (SEQ ID NO: 15) | 1E+04 | 0.346 | 18.6 | |
| | | 1E+05 | 0.379 | 16.8 | |
| | | 1E+06 | 0.564 | 14.5 | |
| LA2 | T7 provider (SEQ ID NO: 2) | 0 | 0.091 | 28.2 | Sensitivity @ 1E+02 copies w/better separation |
| | Blocker (SEQ ID NO: 29) | 1E+02 | 0.311 | 29.8 | |
| | Torch (SEQ ID NO: 50) | 1E+03 | 0.335 | 25.8 | |
| | Non-T7 primer (SEQ ID NO: 22) | 1E+04 | 0.331 | 22.9 | |
| | | 1E+05 | 0.336 | 20.4 | |
| | | 1E+06 | 0.476 | 18.2 | |
| Combo A | T7 provider (SEQ ID NO: 2) | 0 | 0.024 | | Lower RFU & later TTime @ 0 copies |
| | Blocker (SEQ ID NO: 29) | 1E+03 | 0.218 | 31.8 | |
| | Torch (SEQ ID NO: 56) | 1E+06 | 0.303 | 21.6 | |
| | Non-T7 primer (SEQ ID NO: 22) | | | | |
| Combo B | T7 provider (SEQ ID NO: 2) | 0 | 0.020 | 37.0 | Lower RFU & later TTime @ 0 copies |
| | Blocker (SEQ ID NO: 29) | 1E+03 | 0.243 | 32.6 | |
| | Torch (SEQ ID NO: 51) | 1E+06 | 0.323 | 22.2 | |
| | Non-T7 primer (SEQ ID NO: 22) | | | | |
| Combo C | T7 provider (SEQ ID NO: 2) | 0 | 0.025 | | RFUs too low @ other copy levels |
| | Blocker (SEQ ID NO: 29) | 1E+03 | 0.150 | 30.8 | |
| | Torch (SEQ ID NO: 49) | 1E+06 | 0.205 | 21.1 | |
| | Non-T7 primer (SEQ ID NO: 22) | | | | |
| Combo D | T7 provider (SEQ ID NO: 2) | 0 | 0.128 | 34.9 | |
| | Blocker (SEQ ID NO: 29) | 1E+03 | 0.176 | 30.8 | |
| | Torch (SEQ ID NO: 50) | 1E+06 | 0.332 | 20.3 | |
| | Non-T7 primer (SEQ ID NO: 22) | | | | |
| Combo E | T7 provider (SEQ ID NO: 2) | 0 | 0.206 | 35.1 | |
| | Blocker (SEQ ID NO: 29) | 1E+03 | 0.312 | 31.9 | |
| | Torch (SEQ ID NO: 47) | 1E+06 | 0.328 | 20.7 | |
| | Non-T7 primer (SEQ ID NO: 22) | | | | |

TABLE 12-continued

Summary Table for various Non-T7 primer and Torch combinations

| Oligo Set | Oligo Description (ID) | Copies Pae rRNA | Ave Range (RFU) | TTime (min) | Comments |
|---|---|---|---|---|---|
| Combo F | T7 provider (SEQ ID NO: 2) | 0 | 0.119 | 36.5 | |
| | Blocker (SEQ ID NO: 29) | 1E+03 | 0.391 | 33.2 | |
| | Torch (SEQ ID NO: 47) | 1E+06 | 0.486 | 21.9 | |
| | Non-T7 primer (SEQ ID NO: 22) | | | | |
| Combo G | T7 provider (SEQ ID NO: 2) | 0 | 0.250 | 30.6 | |
| | Blocker (SEQ ID NO: 29) | 1E+03 | 0.504 | 30.4 | |
| | Torch (SEQ ID NO: 57) | 1E+06 | 0.664 | 19.8 | |
| | Non-T7 primer (SEQ ID NO: 22) | | | | |
| Combo H | T7 provider (SEQ ID NO: 2) | 0 | 0.023 | 37.9 | Lower RFU |
| | Blocker (SEQ ID NO: 29) | 1E+03 | 0.294 | 33.4 | & later |
| | Torch (SEQ ID NO: 52) | 1E+06 | 0.490 | 23.1 | TTime @ 0 |
| | Non-T7 primer (SEQ ID NO: 22) | | | | copies |

Table 13 summarizes the results from testing different torches for cross-reactions with related organisms. Specificity testing was performed using cell lysates of related organisms *Pseudomonas aeruginosa, Pseudomonas putida, Myroides* sp, *Pseudomonas cepacia, Pseudomonas fluorescens,* and *Pseudomonas pickettii* at ~1E+05 colony forming units (CFU), which is ~1E+08 copies of rRNA.

TABLE 13

Summary of Torches Tested to Check for Cross-Reactions

| Oligo Set | Oligo Description (ID) | CFU @ 1E+05 | Ave Range (RFU) | TTime (min) | Comments |
|---|---|---|---|---|---|
| LA2 | T7 provider (SEQ ID NO: 2) | *P. aeruginosa* | 0.206 | 15.7 | Cross |
| | Blocker (SEQ ID NO: 29) | *P. putida* | 0.235 | 13.6 | reaction w/3 |
| | Torch (SEQ ID NO: 50) | *Myroides* sp. | 0.189 | 12.5 | organisms |
| | Primer (SEQ ID NO: 22) | *P. cepacia* | 0.051 | 30.2 | |
| | | *P. fluorescens* | 0.231 | 17.7 | |
| | | *P. pickettii* | 0.037 | 0.023 | |
| LA2 amp w/ F11 Torch | T7 provider (SEQ ID NO: 2) | *P. aeruginosa* | 0.236 | 18.1 | Cross |
| | Blocker (SEQ ID NO: 29) | *P. putida* | 0.090 | 21.6 | reaction w/2 |
| | Torch (SEQ ID NO: 51) | *Myroides* sp. | 0.118 | 20.5 | organisms |
| | Primer (SEQ ID NO: 22) | *P. cepacia* | 0.033 | | |
| | | *P. fluorescens* | 0.089 | 24.1 | |
| | | *P. pickettii* | 0.026 | 0.036 | |

Example 5

Evaluation of Specific vs. Non-Specific Target Capture

Specific target capture (TC) oligonucleotides, SEQ ID NO:66-71, and specific TC helper oligonucleotides, SEQ ID NO:72 & 73, were designed to target *Pseudomonas aeruginosa* nucleic acid. A non-specific capture oligonucleotide, SEQ ID NO:65, having a random 2'-methoxy poly-(k) sequence with a poly-dT$_3$dA$_{30}$ tail, (k)$_{18}$-dT$_3$dA$_{30}$, where "k" is a random assortment of guanine (G) and uracil (U) or thymine (T) bases incorporated into the oligonucleotide, was also synthesized.

TABLE 14

Target Capture Oligonucleotides

| Oligo Description | SEQ ID NO: | Sequence (5'-3') |
|---|---|---|
| Non-Specific Target Capture | 65 | (k)$_{18}$ TTTAAAAAAAAAAAAAAAAAAAAAAAAAAAAAA |
| Target Capture | 66 | GCTCCTCTACCGCGTCACTTACGTGACACC TTTAAAAAAAAAAAAAAAAAAAAAAAAAAAAAA |
| Target Capture | 67 | ccgcgucacuuacgugacacc TTTAAAAAAAAAAAAAAAAAAAAAAAAAAAAAA |

TABLE 14-continued

Target Capture Oligonucleotides

| Oligo Description | SEQ ID NO: | Sequence (5'-3') |
|---|---|---|
| Target Capture | 68 | cuaccgcgucacuuacg-TTTAAAAAAAAAAAAAAAAAAAAAAAAAAAAA |
| Target Capture | 69 | gcuccucuaccgcgucacuuacg-TTTAAAAAAAAAAAAAAAAAAAAAAAAAAAAA |
| Target Capture | 70 | CCCATTGTCGTTACTCATGTCAGCATTCGC TTTAAAAAAAAAAAAAAAAAAAAAAAAAAAAA |
| Target Capture | 71 | GCTTTTCACACCCATTGTCGTTACTCATGTCAGC TTTAAAAAAAAAAAAAAAAAAAAAAAAAAAAA |
| TC-Helper | 72 | cgcagcuucggugugugguuugagc X |
| TC Helper | 73 | cucaacucaccuucacaggcuuacagaac X |

The specific target capture oligos and helper oligos for *Pseudomonas aeruginosa* nucleic acid and were compared to non-specific target capture. Table 15 shows a summary of exemplary results obtained using specific target capture and helper oligos versus non-specific target capture oligo.

TABLE 15

Summary Table of Specific vs. Non-Specific Target Capture Oligos

| Oligo Set/ Description (ID) | Copies Pae rRNA | Ave Range (RFU) | TTime (min) | Comments |
|---|---|---|---|---|
| Non-specific TC (SEQ ID NO: 65) | 0 | 0.053 | 6.7 | |
| | 1E+04 | 0.188 | 21.4 | |
| TC (SEQ ID NO: 69) | 0 | 0.060 | 8.8 | |
| Helper (SEQ ID NO: 73) | 1E+04 | 0.173 | 20.2 | |
| TC (SEQ ID NO: 68) | 0 | 0.061 | 6.1 | |
| | 1E+04 | 0.166 | 20.4 | |
| TC (SEQ ID NO: 68) | 0 | 0.064 | 8.4 | |
| Helper (SEQ ID NO: 73) | 1E+04 | 0.160 | 21.3 | |

Table 16 shows a summary of results for specific versus non-specific target capture in the presence of *P. putida*. These experiments demonstrated equivalence in performance and specificity between specific target capture oligos and non-specific target capture oligos when testing the capture, amplification and detection of *P. aeruginosa* nucleic acid by itself and in the presence of *P. putida* nucleic acid.

TABLE 16

Summary Table of Specific vs. Non-Specific Target Capture Oligos in the Presence of *P. putida*

| TC Oligo Set/ Description (ID) | Copies Pae rRNA | Ave Range (RFU) | TTime (min) | Comments |
|---|---|---|---|---|
| Non-specific TC (SEQ ID NO: 65) | 0 | 0.057 | 9.0 | |
| | 1E+03 | 0.128 | 20.9 | |
| | 1E+04 | 0.181 | 22.0 | |
| | 1E+*P.putida* | 0.178 | 21.6 | |
| TC (SEQ ID NO: 69) | 0 | 0.059 | 4.7 | |
| Helper (SEQ ID NO: 73) | 1E+03 | 0.119 | 19.1 | |
| | 1E+04 | 0.175 | 20.5 | |
| | 1E+*P.putida* | 0.164 | 20.4 | |
| TC (SEQ ID NO: 68) | 0 | 0.062 | 7.7 | |
| | 1E+03 | 0.095 | 16.9 | |
| | 1E+04 | 0.157 | 20.7 | |
| | 1E+*P.putida* | 0.154 | 19.9 | |
| TC (SEQ ID NO: 68) | 0 | 0.070 | 8.6 | |

TABLE 16-continued

Summary Table of Specific vs. Non-Specific Target Capture Oligos in the Presence of *P. putida*

| TC Oligo Set/ Description (ID) | Copies Pae rRNA | Ave Range (RFU) | TTime (min) | Comments |
|---|---|---|---|---|
| Helper (SEQ ID NO: 73) | 1E+03 | 0.091 | 6.4 | |
| | 1E+04 | 0.142 | 19.5 | |
| | 1E+*P.putida* | 0.141 | 20.4 | |

Example 6

Reducing Cross-Reactivity with Organisms Related to *Pseudomonas Aeruginosa*

This Example describes additional experiments performed in an effort to reduce cross-reactivity and amplification of organisms closely related to *Pseudomonas aeruginosa*. An exemplary graphical presentation of real-time assay data showing the signal obtained for 10 CFUs of *P. aeruginosa* as compared to $10^5$ CFU levels of closely related pseudomonads, *P. stutzeri*, *P. pseudoalcaligenes*, and *P. mendocina*, is shown in FIG. 1.

The AveRange (RFU) and TTime (min) or Cycle Time (min) results are presented in tables below, as opposed to graphic representations. A spreadsheet was created that analyzes the raw data file, and determines positive and negative *P. aeruginosa* results along with assay validity. A positive result is determined using a cutoff value of 750, a relative fluorescence unit (RFU) for the Trimmean cycles 71-76 from the background subtracted data. The validity of the assay, based on the UIC (internal control) results, is only confirmed for negative *P. aeruginosa* results The information provided in Table 17, is a subset of the experiments completed. Table 17 represents testing of lysates of these nearest neighbor *Pseudomonas* organisms, along with some environmental. All experimental results presented used the oligo set shown in Table 17. One colony forming unit (CFU) corresponds to 1000 copies of rRNA. The same ATCC strains identified as three cross-reacting organisms were tested and the results confirmed. Interestingly, when analyzing the graphical representations of these experiments (not shown), amplification with the cross-reacting organisms displayed plateaus.

TABLE 17

Check for Cross-Reactions with *P. aeruginosa* Real Time RTMA

| Oligo Description (ID): | ~1E+05 copies RNA | Results | Validity | Comments |
|---|---|---|---|---|
| Torch (SEQ ID NO: 54) | *P. aeruginosa* | P | 6/6 | Cross reaction w/3 organisms |
| T7 provider (SEQ ID NO: 2) | *P. stutzeri* | P | 3/6 | |
| Blocker (SEQ ID NO: 29) | *P. pseudoalcaligenes* | P | 5/6 | |
| Primer (SEQ ID NO: 24) | *P. mendocina* | P | 6/6 | |
| Extender (SEQ ID NO: 44) | *P. spinosa* | N | 6/6 | |
| Target Capture (SEQ ID NO: 69) | *S. maltophila* | N | 6/6 | |
| TC Helper (SEQ ID NO: 73) | *B. cepacia* | N | 6/6 | |
| | *R. pickettii* | N | 6/6 | |
| | *B. pyrocinia* | N | 6/6 | |
| | Negative Control | N | 6/6 | |

Based on the results from Table 17, the next experiment with the three organisms looked at a titration of CFUs to determine if the same low-level plateau occurs at the different levels.

Table 18 shows the results of the CFU titration as analyzed. The titration shows the same low-level amplification and plateau with only the emergence time varying based on the CFU level (not shown).

TABLE 18

Titration of Cross-Reacting Organisms with *P. aeruginosa* Real Time RTMA

| Organism | ~1E+02 CFU | ~1E+03 CFU | ~1E+04 CFU | ~1E+05 CFU | 1E+04 copies RNA | Validity | Comments |
|---|---|---|---|---|---|---|---|
| *P. aeruginosa* | n/a | n/a | n/a | n/a | P | 6/6 | Cross reaction w/3 organisms at all levels |
| *P. stutzeri* | P/N | P | P | P | n/a | 11/12 | |
| *P. pseudoalcaligenes* | P/N | P | P | P | n/a | 11/12 | |
| *P. mendocina* | P/N | P | P/N | P | n/a | 12/12 | |
| Negative Control | n/a | n/a | n/a | n/a | n/a | 6/6 | |

The next experiment (Table 19) focused on assessing the *Pseudomonas aeruginosa* result in the presence of one of these cross-reacting organisms. In previous specificity experiments, *P. putida* cross reacted with a different oligo set than the final one chosen, so it was used as an additional control to look at *Pseudomonas aeruginosa* recovery. The results show the *Pseudomonas aeruginosa* signal is partially suppressed as the CFU level of *P. putida* increases (not shown), but greater inhibition of *Pseudomonas aeruginosa* was seen with *P. mendocina*, which was not expected. The Pos/Neg results for *P. putida* in Table 19 were low-level positives and not inconsistent when comparing replicates from the same target capture reaction.

TABLE 19

Titration of Cross-Reacting Organisms and *P. aeruginosa* Recovery

| Organism | ~1E+02 CFU | ~1E+03 CFU | ~1E+04 CFU | ~1E+05 CFU | 1E+04 copies RNA | Validity | Comments |
|---|---|---|---|---|---|---|---|
| *P. aeruginosa* (Pae) | n/a | n/a | n/a | n/a | P | 12/12 | |
| *P. putida* | P/N | N | P/N | N | n/a | 23/24 | Suppression of Pae signal |
| *P. putida* + Pae | P | P | P | P | n/a | 24/24 | |
| *P. mendocina* | P | P | P | P | n/a | 24/24 | Inhibition of Pae signal |
| *P. mendocina* + Pae | P | P | P | P | n/a | 24/24 | |
| Negative Control | n/a | n/a | n/a | n/a | n/a | 12/12 | |

Based on sequence comparison of the *P. mendocina* with Pae and *P. putida*, complete inhibition of *Pseudomonas aeruginosa* amplification should not have occurred, so the experiment was repeated with all three cross reacting organisms and analyzed with the TTime algorithm (Table 20). As expected, *Pseudomonas aeruginosa* amplification does occur in the presence of these other organisms as opposed to the first result, with the *Pseudomonas aeruginosa* RFU signal only being partially suppressed.

TABLE 20

Cross-Reacting Organisms and P. aeruginosa Recovery

| Organism | ~Copies RNA | Ave Range (RFU) | TTime (min) | Comments |
|---|---|---|---|---|
| P. aeruginosa (Pae) | 0 | 0.077 | 64.3 | |
| P. aeruginosa | 1E+06 | 0.873 | 15.8 | |
| P. stutzeri | 1E+06 | 0.127 | 15.1 | Low level cross reaction |
| P. stutzeri + Pae | 1E+06 | 0.504 | 15.3 | Suppression of Pae signal |
| P. pseudoalcaligenes | 1E+06 | 0.121 | 13.5 | Low level cross reaction |
| P. pseudoalcaligenes + Pae | 1E+06 | 0.385 | 14.8 | Suppression of Pae signal |
| P. mendocina | 1E+06 | 0.113 | 17.6 | Low level cross reaction |
| P. mendocina + Pae | 1E+06 | 0.792 | 15.3 | Suppression of Pae signal |

The results shown were tested using cell lysates with the exception of Pseudomonas aeruginosa, which was done using rRNA. Based on the unexpected results with these lysates, purified RNA from the organisms was used to do a similar Pseudomonas aeruginosa recovery experiment (Table 21). The same cross-reactions were seen with P. stutzeri, P. pseudoalcaligenes and P. mendocina, however there is no suppression of the Pseudomonas aeruginosa signal in the presence of these organism's rRNA at these levels.

TABLE 21

Cross-Reacting Organisms and P. aeruginosa Recovery

| Organism | ~Copies RNA | AveRange (RFU) | TTime (min) | Comments |
|---|---|---|---|---|
| P. aeruginosa (Pae) | 0 | 0.052 | | |
| P. aeruginosa | 1E+04 | 0.400 | 24.4 | |
| P. aeruginosa | 1E+06 | 0.485 | 19.1 | |
| P. stutzeri | 1E+06 | 0.073 | 25.0 | Low level cross reaction |
| P. stutzeri + Pae | 1E+04 | 0.359 | 22.4 | |
| P. stutzeri + Pae | 1E+06 | 0.439 | 17.9 | |
| P. pseudoalcaligenes | 1E+06 | 0.079 | 24.2 | Low level cross reaction |
| P. pseudoalcaligenes + Pae | 1E+04 | 0.370 | 22.5 | |
| P. pseudoalcaligenes + Pae | 1E+06 | 0.497 | 17.6 | |
| P. mendocina | 1E+06 | 0.084 | 24.7 | Low level cross reaction |
| P. mendocina + Pae | 1E+04 | 0.400 | 22.8 | |
| P. mendocina + Pae | 1E+06 | 0.471 | 17.6 | |
| P. aeruginosa (TC) | 0 | 0.058 | 11.7 | Incorrect TTime value |
| P. aeruginosa (TC) | 1E+04 | 0.143 | 25.6 | |
| P. aeruginosa (TC) | 1E+06 | 0.249 | 21.8 | |
| P. stutzeri (TC) | 1E+06 | 0.075 | 19.7 | |
| P. stutzeri + Pae (TC) | 1E+04 | 0.149 | 24.7 | |
| P. stutzeri + Pae (TC) | 1E+06 | 0.243 | 21.6 | |
| P. pseudoalcaligenes (TC) | 1E+06 | 0.072 | 21.9 | |
| P. pseudoalcaligenes + Pae (TC) | 1E+04 | 0.150 | 25.1 | |
| P. pseudoalcaligenes + Pae (TC) | 1E+06 | 0.262 | 21.6 | |
| P. mendocina (TC) | 1E+06 | 0.069 | 17.7 | |
| P. mendocina + Pae (TC) | 1E+04 | 0.174 | 26.0 | |
| P. mendocina + Pae (TC) | 1E+06 | 0.257 | 23.0 | |

These results indicate that the species-specific detection of Pseudomonas aeruginosa can be achieved by the present invention even in the presence of closely related organisms, based upon the characteristics of the real-time TMA data (e.g., the size and shape of RFU curves generated from the real-time TMA reactions). It is therefore possible to use the methods of the present invention to not only detect the presence of Pseudomonas aeruginosa, but also to detect other related organisms that may be present. For example, if the observed RFU value is above a suitable threshold, it could be concluded that the sample contains Pseudomonas aeruginosa, and if lower RFU values are observed within a range determined to be indicative of the presence of other closely related organisms, then it can be conclude that the sample also contains one or more of these closely related organisms. Thus, the methods of the invention may be used in the simultaneous/differential detection of Pseudomonas aeruginosa and one or more of these related organisms, based upon the distinct TMA signal characteristics exhibited by the organisms.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An oligonucleotide set for use in a transcription-based nucleic acid amplification assay to detect if *Pseudomonas aeruginosa* is present in a sample, the oligonucleotide set comprising a T7 provider oligo up to 100 nucleotide residues in length and a non-T7 primer oligo up to 50 nucleotide residues in length, wherein the T7 provider oligo targets the complement of a sequence in a region of *Pseudomonas aeruginosa* 23s rRNA and comprises a nucleic acid sequence consisting of SEQ ID NO:2, SEQ ID NO:1, SEQ ID NO:11, or SEQ ID NO:14, and where the non-T7 primer oligo comprises a nucleic acid sequence selected from the group consisting of SEQ ID NO:22, SEQ ID NO:19, and SEQ ID NO:15, wherein the oligonucleotide set allows transcription-based amplification of a desired region of *Pseudomonas aeruginosa* 23S rRNA if present in the sample.

2. The oligonucleotide set of claim 1, wherein:
   a) the T7 provider oligo comprises a nucleic acid sequence of SEQ ID NO:11 and the non-T7 primer oligo comprises a nucleic acid sequence of SEQ ID NO:19;
   b) the T7 provider oligo comprises a nucleic acid sequence of SEQ ID NO:14 and the non-T7 primer oligo comprises a nucleic acid sequence of SEQ ID NO:15;
   c) the T7 provider oligo comprises a nucleic acid sequence of SEQ ID NO:2 and the non-T7 primer oligo comprises a nucleic acid sequence of SEQ ID NO:22; or
   d) the T7 provider oligo comprises a nucleic acid sequence of SEQ ID NO:1 and the non-T7 primer oligo comprises a nucleic acid sequence of SEQ ID NO:22.

3. The oligonucleotide set of claim 1, further comprising a detection oligo.

4. The oligonucleotide set of claim 3, where the detection oligo is a torch oligo or molecular beacon.

5. The oligonucleotide set of claim 4, wherein:
   a) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:50;
   b) the T7 provider oligo comprises a nucleic acid sequence of SEQ ID NO:11, the non-T7 primer oligo comprises a nucleic acid sequence of SEQ ID NO:19, and the torch oligo comprises a nucleic acid sequence of SEQ ID NO:56;
   c) the T7 provider oligo comprises a nucleic acid sequence of SEQ ID NO:14, the non-T7 primer oligo comprises a nucleic acid sequence of SEQ ID NO:15, and the torch oligo comprises a nucleic acid sequence of SEQ ID NO:51;

d) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:51;
e) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:54; or
f) the T7 provider oligo comprises a nucleic acid sequence of SEQ ID NO:1, the non-T7 primer oligo comprises a nucleic acid sequence of SEQ ID NO:22, and the torch oligo comprises a nucleic acid sequence of SEQ ID NO:54.

6. The oligonucleotide set of claim 4, further comprising a blocker oligo.

7. The oligonucleotide set of claim 6, wherein:
a) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:50, and the blocker oligo comprises the nucleic acid sequence of SEQ ID NO:29;
b) the T7 provider oligo comprises a nucleic acid sequence of SEQ ID NO:11, the non-T7 primer oligo comprises a nucleic acid sequence of SEQ ID NO:19, the torch oligo comprises a nucleic acid sequence of SEQ ID NO:56, and the blocker oligo comprises the nucleic acid sequence of SEQ ID NO:40;
c) the T7 provider oligo comprises a nucleic acid sequence of SEQ ID NO:14, the non-T7 primer oligo comprises a nucleic acid sequence of SEQ ID NO:15, the torch oligo comprises a nucleic acid sequence of SEQ ID NO:51, and the blocker oligo comprises the nucleic acid sequence of SEQ ID NO:42;
d) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:51, and the blocker oligo comprises the nucleic acid sequence of SEQ ID NO:29;
e) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:54, and the blocker oligo comprises the nucleic acid sequence of SEQ ID NO:29; or
f) the T7 provider oligo comprises a nucleic acid sequence of SEQ ID NO:1, the non-T7 primer oligo comprises a nucleic acid sequence of SEQ ID NO:22, the torch oligo comprises a nucleic acid sequence of SEQ ID NO:54, and the blocker oligo comprises the nucleic acid sequence of SEQ ID NO:26.

8. The oligonucleotide set of claim 1, further comprising an extend oligo.

9. The oligonucleotide set of claim 8, where the extend oligo comprises the nucleic acid sequence selected from SEQ ID NO:43, or SEQ ID NO:44.

10. An oligonucleotide set for use in a transcription-based nucleic acid amplification assay to detect if *Pseudomonas aeruginosa* is present in a sample, the oligonucleotide set comprising a T7 provider oligo up to 100 nucleotide residues in length that comprises the nucleic acid sequence of SEQ ID NO:2 and a non-T7 oligo having a nucleotide sequence consisting of the nucleic acid sequence of SEQ ID NO:24, and optionally, further comprising a blocker oligo that comprises the nucleic acid sequence of SEQ ID NO:29, a torch oligo that comprises the nucleic acid sequence of SEQ ID NO:54, an extend oligo that comprises the nucleic acid sequence of SEQ ID NO:44, a target capture oligo that comprises the nucleic acid sequence of SEQ ID NO:69 and, optionally, a target capture helper oligo that comprises the nucleic acid sequence of SEQ ID NO:73, wherein the oligonucleotide set allows transcription-based amplification of a desired region of *Pseudomonas aeruginosa* 23S rRNA if present in the sample.

11. A kit for use in a transcription-based nucleic acid amplification assay to detect if *Pseudomonas aeruginosa* is present in a sample, the kit comprising: (a) an oligonucleotide set comprising a T7 provider oligo up to 100 nucleotide residues in length and a non-T7 primer oligo up to 50 nucleotide residues in length, wherein the T7 provider oligo targets the complement of a sequence in a region of *Pseudomonas aeruginosa* 23s rRNA and comprises a nucleic acid sequence consisting of SEQ ID NO:2, SEQ ID NO:1, SEQ ID NO:11, or SEQ ID NO:14, and where the non-T7 primer oligo comprises a nucleic acid sequence selected from the group consisting of SEQ ID NO:22, SEQ ID NO:19, and SEQ ID NO:15, wherein the oligonucleotide set allows transcription-based amplification of a desired region of *Pseudomonas aeruginosa* 23S rRNA if present in the sample, and (b) one or more of reverse transcriptase and RNA polymerase.

12. The kit of claim 11, where the non-T7 primer targets a sequence in a region of *Pseudomonas aeruginosa* nucleic acid corresponding to bases 900-950 of *E. coli* 23s rRNA.

13. The kit of claim 11, where the non-T7 primer targets a sequence in a region of *Pseudomonas aeruginosa* nucleic acid corresponding to bases 918-943 of *E. coli* 23s rRNA.

14. The kit of claim 11, wherein:
a) the T7 provider oligo comprises a nucleic acid sequence of SEQ ID NO:11 and the non-T7 primer oligo comprises a nucleic acid sequence of SEQ ID NO:19;
b) the T7 provider oligo comprises a nucleic acid sequence of SEQ ID NO:14 and the non-T7 primer oligo comprises a nucleic acid sequence of SEQ ID NO:15;
c) the T7 provider oligo comprises a nucleic acid sequence of SEQ ID NO:2 and the non-T7 primer oligo comprises a nucleic acid sequence of SEQ ID NO:22; or
d) the T7 provider oligo comprises a nucleic acid sequence of SEQ ID NO:1 and the non-T7 primer oligo comprises a nucleic acid sequence of SEQ ID NO:22.

15. The kit of claim 11, further comprising a detection oligo.

16. The kit of claim 15, where the detection oligo is a torch oligo or molecular beacon.

17. The kit of claim 16, wherein:
a) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:50;
b) the T7 provider oligo comprises a nucleic acid sequence of SEQ ID NO:11, the non-T7 primer oligo comprises a nucleic acid sequence of SEQ ID NO:19, and the torch oligo comprises a nucleic acid sequence of SEQ ID NO:56;
c) the T7 provider oligo comprises a nucleic acid sequence of SEQ ID NO:14, the non-T7 primer oligo comprises a nucleic acid sequence of SEQ ID NO:15, and the torch oligo comprises a nucleic acid sequence of SEQ ID NO:51;
d) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:51;
e) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:54; or
f) the T7 provider oligo comprises a nucleic acid sequence of SEQ ID NO:1, the non-T7 primer oligo comprises a nucleic acid sequence of SEQ ID NO:22, and the torch oligo comprises a nucleic acid sequence of SEQ ID NO:54.

18. The kit of claim 16, further comprising a blocker oligo.

19. The kit of claim 18, wherein:
a) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:50, and the blocker oligo comprises the nucleic acid sequence of SEQ ID NO:29;
b) the T7 provider oligo comprises a nucleic acid sequence of SEQ ID NO:11, the non-T7 primer oligo comprises a nucleic acid sequence of SEQ ID NO:19, the torch oligo comprises a nucleic acid sequence of SEQ ID NO:56, and the blocker oligo comprises the nucleic acid sequence of SEQ ID NO:40;
c) the T7 provider oligo comprises a nucleic acid sequence of SEQ ID NO:14, the non-T7 primer oligo comprises a nucleic acid sequence of SEQ ID NO:15, the torch oligo comprises a nucleic acid sequence of SEQ ID NO:51, and the blocker oligo comprises the nucleic acid sequence of SEQ ID NO:42;
d) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:51, and the blocker oligo comprises the nucleic acid sequence of SEQ ID NO:29;
e) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:54, and the blocker oligo comprises the nucleic acid sequence of SEQ ID NO:29; or
f) the T7 provider oligo comprises a nucleic acid sequence of SEQ ID NO:1, the non-T7 primer oligo comprises a nucleic acid sequence of SEQ ID NO:22, the torch oligo comprises a nucleic acid sequence of SEQ ID NO:54, and the blocker oligo comprises the nucleic acid sequence of SEQ ID NO:26.

20. The kit of claim 11, further comprising an extend oligo.

21. The kit of claim 20, where the extend oligo comprises a nucleic acid sequence selected from SEQ ID NO:43 or SEQ ID NO:44.

22. A kit for use in a transcription-based nucleic acid amplification assay to detect if *Pseudomonas aeruginosa* is present in a sample, the kit comprising: (a) an oligonucleotide set comprising a T7 provider oligo up to 100 nucleotide residues in length that comprises the nucleic acid sequence of SEQ ID NO:2 and a non-T7 primer oligo having a nucleotide sequence consisting of the nucleic acid sequence of SEQ ID NO:24, and, optionally, further comprising a blocker oligo that comprises the nucleic acid sequence of SEQ ID NO:29, a torch oligo that comprises the nucleic acid sequence of SEQ ID NO:54, an extend oligo that comprises the nucleic acid sequence of SEQ ID NO:44, a target capture oligo that comprises the nucleic acid sequence of SEQ ID NO:69 and, optionally, a target capture helper oligo that comprises the nucleic acid sequence of SEQ ID NO:73, wherein the oligonucleotide set allows transcription-based amplification of a desired region of *Pseudomonas aeruginosa* 23S rRNA if present in the sample, and (b) one or more of reverse transcriptase and RNA polymerase.

23. A method for detecting the presence of *Pseudomonas aeruginosa* in a sample, the method comprising performing a transcription-based nucleic acid amplification assay using an oligonucleotide set comprising a T7 provider oligo up to 100 nucleotide residues in length and a non-T7 primer oligo up to 50 nucleotide residues in length, wherein the T7 provider oligo targets the complement of a sequence in a region of *Pseudomonas aeruginosa* 23s rRNA and comprises a nucleic acid sequence selected from the group consisting of SEQ ID NO:2, SEQ ID NO:1, SEQ ID NO:11, and SEQ ID NO:14, and where the non-T7 primer oligo comprises a nucleic acid sequence selected from the group consisting of SEQ ID NO:22, SEQ ID NO:19, and SEQ ID NO:15, wherein the oligonucleotide set allows transcription-based amplification of a desired region of *Pseudomonas aeruginosa* 23S rRNA if present in the sample.

24. The method of claim 23, wherein:
a) the T7 provider oligo comprises a nucleic acid sequence of SEQ ID NO:11 and the non-T7 primer oligo comprises a nucleic acid sequence of SEQ ID NO:19;
b) the T7 provider oligo comprises a nucleic acid sequence of SEQ ID NO:14 and the non-T7 primer oligo comprises a nucleic acid sequence of SEQ ID NO:15;
c) the T7 provider oligo comprises a nucleic acid sequence of SEQ ID NO:2 and the non-T7 primer oligo comprises a nucleic acid sequence of SEQ ID NO:22; or
d) the T7 provider oligo comprises a nucleic acid sequence of SEQ ID NO:1 and the non-T7 primer oligo comprises a nucleic acid sequence of SEQ ID NO:22.

25. The method of claim 23, further comprising detecting amplified nucleic acid with a detection oligo.

26. The method of claim 25, where the detection oligo is a torch oligo or molecular beacon.

27. The method of claim 26, wherein:
a) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:50;
b) the T7 provider oligo comprises a nucleic acid sequence of SEQ ID NO:11, the non-T7 primer oligo comprises a nucleic acid sequence of SEQ ID NO:19, and the torch oligo comprises a nucleic acid sequence of SEQ ID NO:56;
c) the T7 provider oligo comprises a nucleic acid sequence of SEQ ID NO:14, the non-T7 primer oligo comprises a nucleic acid sequence of SEQ ID NO:15, and the torch oligo comprises a nucleic acid sequence of SEQ ID NO:51;

d) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:51;

e) the T7 provider oligo comprises a nucleic acid sequence of SEQ ID NO:2, the non-T7 primer oligo comprises a nucleic acid sequence of SEQ ID NO:22, and the torch oligo comprises a nucleic acid sequence of SEQ ID NO:54; or f) the T7 provider oligo comprises a nucleic acid sequence of SEQ ID NO:1, the non-T7 primer oligo comprises a nucleic acid sequence of SEQ ID NO:22, and the torch oligo comprises a nucleic acid sequence of SEQ ID NO:54.

28. The method of claim 26, further comprising a blocker oligo.

29. The method of claim 28, wherein:

a) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:50, and the blocker oligo comprises the nucleic acid sequence of SEQ ID NO:29;

b) the T7 provider oligo comprises a nucleic acid sequence of SEQ ID NO:11, the non-T7 primer oligo comprises a nucleic acid sequence of SEQ ID NO:19, the torch oligo comprises a nucleic acid sequence of SEQ ID NO:56, and the blocker oligo comprises the nucleic acid sequence of SEQ ID NO:40;

c) the T7 provider oligo comprises a nucleic acid sequence of SEQ ID NO:14, the non-T7 primer oligo comprises a nucleic acid sequence of SEQ ID NO:15, the torch oligo comprises a nucleic acid sequence of SEQ ID NO:51, and the blocker oligo comprises the nucleic acid sequence of SEQ ID NO:42;

d) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:51, and the blocker oligo comprises the nucleic acid sequence of SEQ ID NO:29;

e) the T7 provider oligo comprises a nucleic acid sequence of SEQ ID NO:2, the non-T7 primer oligo comprises a nucleic acid sequence of SEQ ID NO:22, the torch oligo comprises a nucleic acid sequence of SEQ ID NO:54, and the blocker oligo comprises the nucleic acid sequence of SEQ ID NO:29; or f) the T7 provider oligo comprises a nucleic acid sequence of SEQ ID NO:1, the non-T7 primer oligo comprises a nucleic acid sequence of SEQ ID NO:22, the torch oligo comprises a nucleic acid sequence of SEQ ID NO:54, and the blocker oligo comprises the nucleic acid sequence of SEQ ID NO:26.

30. The method of claim 29, further comprising a target capture oligo comprising the nucleic acid sequence of SEQ ID NO:69 and, optionally, a target capture helper oligo comprising the nucleic acid sequence of SEQ ID NO:73.

31. The method of claim 26 wherein detecting said amplified nucleic acid occurs in real-time.

32. The method of claim 31 wherein *P. aeruginosa* nucleic acid is specifically detected in the presence of closely related Pseudomonads.

33. The method of claim 31 wherein the detection cut-off is set whereby *P. aeruginosa* nucleic acid and one or more closely related but not all Pseudomonads are detected.

34. The method of claim 23, further comprising an extend oligo.

35. The method of claim 34, where the extend oligo comprises the nucleic acid sequence selected from the group consisting of SEQ ID NO:43 and SEQ ID NO:44.

36. An oligonucleotide set for detecting *Pseudomonas aeruginosa* in a sample, the oligonucleotide set comprising two amplification oligonucleotides designed to amplify *Pseudomonas aeruginosa* 23s ribosomal nucleic acid in a region corresponding to nucleobase positions 700 to 1000 of *E. coli* 23S rRNA, wherein the amplification oligomers are a promoter provider oligo up to 100 nucleotide residues in length comprising a nucleic acid sequence selected from the group consisting of: SEQ ID NOs: 2, 11, and 14, and a non-promoter primer oligo up to 50 nucleotide residues in length comprising a nucleic acid sequence selected from the group consisting of: SEQ ID NOs: 22, 19, and 15, wherein the oligonucleotide set allows transcription-based amplification of a desired region of *Pseudomonas aeruginosa* 23S rRNA if present in the sample.

37. The oligonucleotide set of claim 36, further comprising one or more probes for detecting *Pseudomonas aeruginosa* 23s ribosomal nucleic acid.

38. A method for detecting the presence of *Pseudomonas aeruginosa* in a sample, said method comprising performing a transcription-based nucleic acid amplification assay using the amplification oligonucleotides of claim 36 to form nucleic acid amplification products, and detecting the amplified nucleic acid products with one or more oligonucleotide probes that target a region within the amplified nucleic acid products.

* * * * *